(12) United States Patent
Sem

(10) Patent No.: US 7,807,399 B2
(45) Date of Patent: Oct. 5, 2010

(54) METHODS FOR DETECTING THIOL-CONTAINING NUCLEOTIDE DIPHOSPHATES WITH THIOL-REACTIVE FLUORESCENT REAGENTS

(75) Inventor: Daniel S. Sem, New Berlin, WI (US)

(73) Assignee: Marquette University, Milwaukee, WI (US)

( * ) Notice: Subject to any disclaimer, the term of this patent is extended or adjusted under 35 U.S.C. 154(b) by 0 days.

(21) Appl. No.: 12/501,967

(22) Filed: Jul. 13, 2009

(65) Prior Publication Data

US 2009/0325179 A1 Dec. 31, 2009

Related U.S. Application Data

(63) Continuation of application No. 11/512,832, filed on Aug. 30, 2006, now Pat. No. 7,585,643.

(60) Provisional application No. 60/715,090, filed on Sep. 8, 2005.

(51) Int. Cl.
*C12Q 1/34* (2006.01)
(52) U.S. Cl. .............................. 435/18; 435/15; 435/21
(58) Field of Classification Search .................. 435/18, 435/15, 21
See application file for complete search history.

(56) References Cited

U.S. PATENT DOCUMENTS

| 7,585,643 B2 * | 9/2009 | Sem ............................ 435/15 |
| 2007/0054410 A1 * | 3/2007 | Sem et al. .................... 436/120 |

OTHER PUBLICATIONS

Cohen, Philip, "The Origins of Protein Phosphorylation", Nature Cell Biology, vol. 4, May 2002, pp. E127-E130.
Cohen, Philip, "The Role of Protein Phosphorylation in Human Health and Disease", The Sir Hans Krebs Medal Lecture, Delivered on Jun. 30, 2001 at the FEBS Meeting in Lisbon, MRC Protein Phosphorylation Unit, School of Life Sciences, University of Dundee, Scotland; Eur. J. Biochem 268, pp. 5001-5010 (2001).
Hanks, Steven K. and Hunter, Tony, "The Eukaryotic Protein Kinase Superfamily: Kinase (Catalytic) Domain Structure and Classification", Protein Kinases 6, The FASEB Journal, vol. 9, May 1995, pp. 576-596.
Marras, Salvatore A. E., Kramer, Fred Russell, and Tyagi, Sanjay, "Efficiencies of Fluorescence Resonance Energy Transfer and Contact-Mediated Quenching in Oligonucleotide Probes", Nucleic Acids Research, 2002, vol. 30, No. 21, e122, pp. 1-8.
Nick, Jerry A. et al, "Role of p38 Mitogen-Activated Protein Kinase in a Murine Model of Pulmonary Inflammation", The Journal of Immunology, 2000, 164: pp. 2151-2159.
Zaman, G. J. R., Garritsen, A., De Boer, TH., and Van Boeckel C. A. A., "Fluorescence Assays for High-Throughput Screening of Protein Kinases", Combinatorial Chemistry & High Throughput Screening, 2003, vol. 6, No. 4, pp. 313-320.
Xia, Wensheng et al, "Applications of Fluorescent Polymer Superquenching to High Throughput Screening Assays for Protein Kinases", Assay and Drug Development Technologies, vol. 2, No. 2, 2004, pp. 183-192.
Blume-Jensen, Peter and Hunter, Tony, "Oncogenic Kinase Signalling", Nature, vol. 411, May 17, 2001, pp. 355-365.
Manning, G., Whyte, D. B., Martinez, R., Hunter, T., and Sudarsanam, S., "The Protein Kinase Complement of the Human Genome", Science, Dec. 6, 2002, vol. 298, pp. 1912-1916, 1933-1934.
Daly, Thomas J., Olson, John S., and Matthews, Kathleen Shive, "Formation of Mixed Disulfide Adducts at Cysteine-281 of the Lactose Repressor Protein Affects Operator and Inducer Binding Parameters", Biochemistry, 1986, vol. 25, pp. 5468-5474.
Ways, D. Kirk, and Sheetz, Matthew J., "The Role of Protein Kinase C in the Development of the Complications of Diabetes", Vitamins and Hormones, vol. 60, pp. 149-193, Copyright © 2001.
Eckstein, Fritz and Goody, Roger S., "Synthesis and Properties of Diastereoisomers of Adenosine 5'-(O-1-Thiotriphosphate) and Adenosine 5'-(O-2-Thiotriphosphate)" Biochemistry, vol. 15, No. 8, 1976, pp. 1685-1691.
Viola, Ronald E., Raushel, Frank M., Rendina, Alan R., and Cleland, W. W., "Substrate Synergism and the Kinetic Mechanism of Yeast Hexokinase", Biochemistry, 1982, vol. 21, pp. 1295-1302.
Pullela, Phani Kumar, Chiku, Taurai, and Sem, Daniel S., "Fluorescence Probes with Utility in Kinase Assay and Redox Sensing", The FASEB Journal, Mar. 4, 2005, vol. 19, No. 4, Experimental Biology/IUPS 2005: Meeting Abstracts, p. A265.
Invitrogen Product Description for BODIPY® FL L-cystine available at least as early as Jan. 1, 2003.
Chiku, Taurai, Pullela, Phani Kumar, and Sem, Daniel S., "A Dithio-Coupled Kinase and ATPase Assay", Journal of Biomolecular Screening (X)X; 2006, pp. 1-10.
Chiku, Taurai, Pullela, Phani Kumar, and Sem, Daniel S., "A General Dithiol-Coupled UV Vis and Fluorescence Assay for Kinases", FASEB Journal, 19 (4, Part 1 Suppl.) A265-266, Abstract 212.4, 2005.
Churchich, Jorge E. and Wu, Christine, "Nucleoside Phosphorothioates As Probes of the Nucleotide Binding Site of Brain Pyridoxal Kinase", The Journal of Biological Chemistry, vol. 257, No. 20, Oct. 25, 1982, pp. 12136-12140.
Kupcho, Kevin, Somberg, Richard, Bulleit, Bob, and Goueli, Said A., "A Homogeneous, Nonradioactive High-Throughput Fluorogenic Protein Kinase Assay", Analytical Biochemistry, 317 (2003) pp. 210-217.
Pullela, Phani Kumar, Chiku, Taurai, Carvan, Michael J. (III), and Sem, Daniel S., "Fluorescence-Based Detection of Thiols in Vitro and in Vivo Using Dithiol Probes", Analytical Biochemistry, 352 (2006) pp. 265-273.

* cited by examiner

*Primary Examiner*—Ralph Gitomer
(74) *Attorney, Agent, or Firm*—Andrus, Sceales, Starke & Sawall, LLP

(57) ABSTRACT

Disclosed are methods for detecting thiol-containing nucleotide diphosphates. The methods utilize thiol-reactive fluorescent reagents.

21 Claims, 24 Drawing Sheets

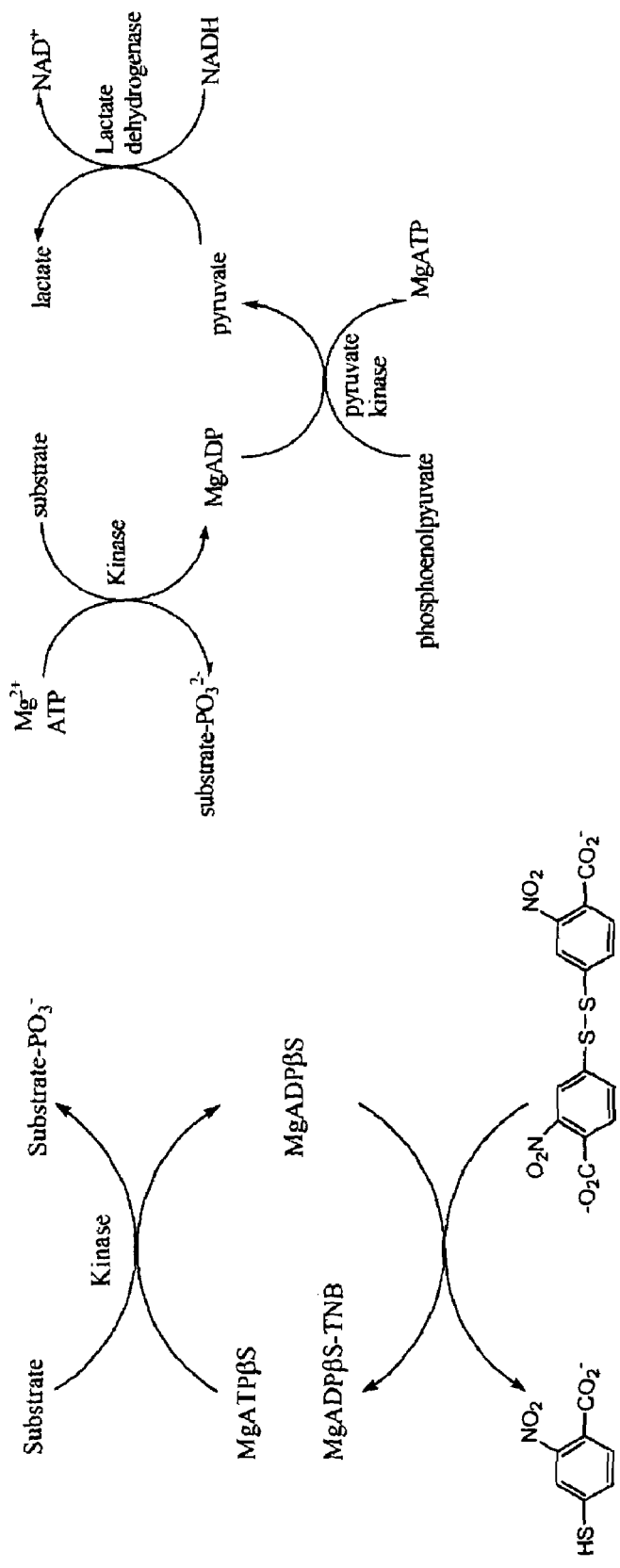
Figure 1. DTNB-coupled general kinase assay (left) and PK/LDH-coupled kinase assay (right)

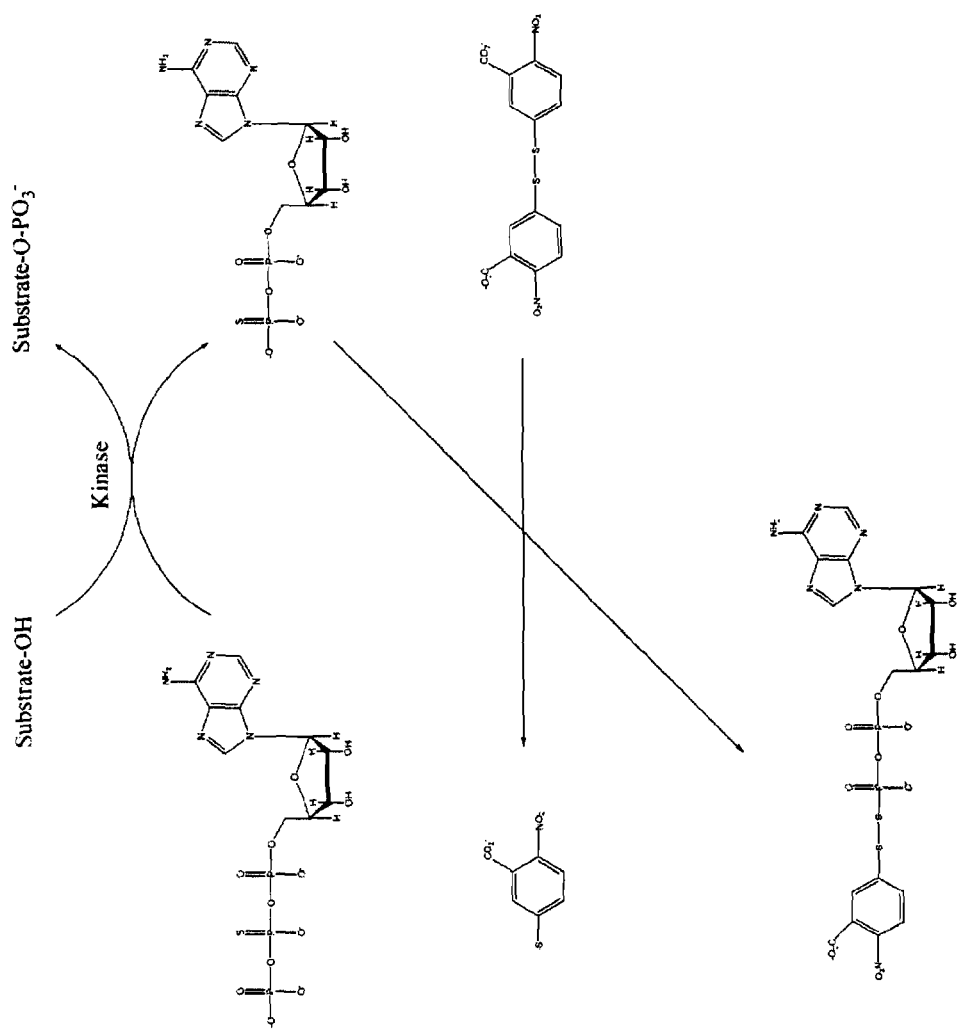
Figure 2. Schematic representation of DTNB-coupled reaction.

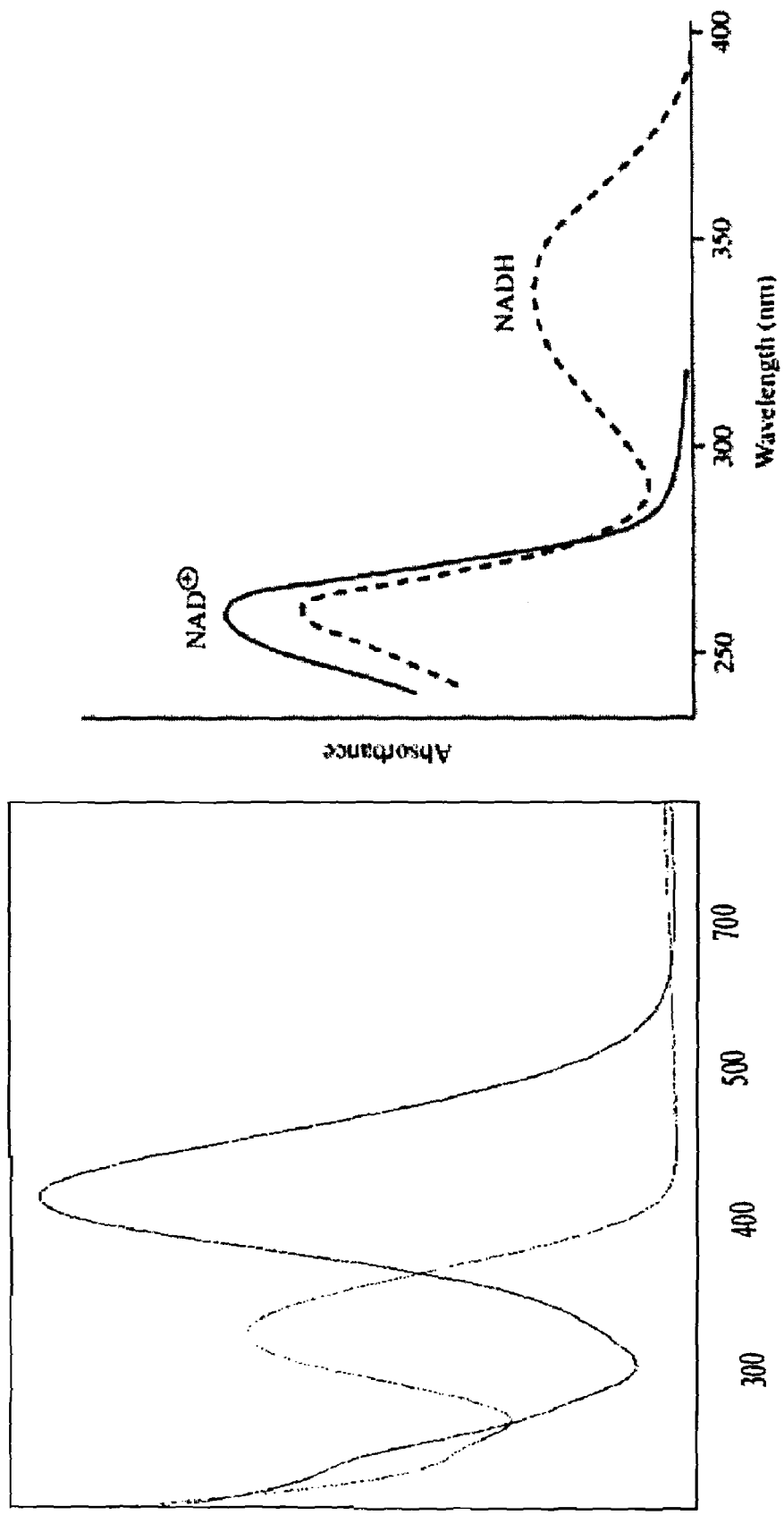
Figure 3. Bathochromic shift in UV-visible absorption spectra of DTNB (left) and NAD(P) (right) after reduction

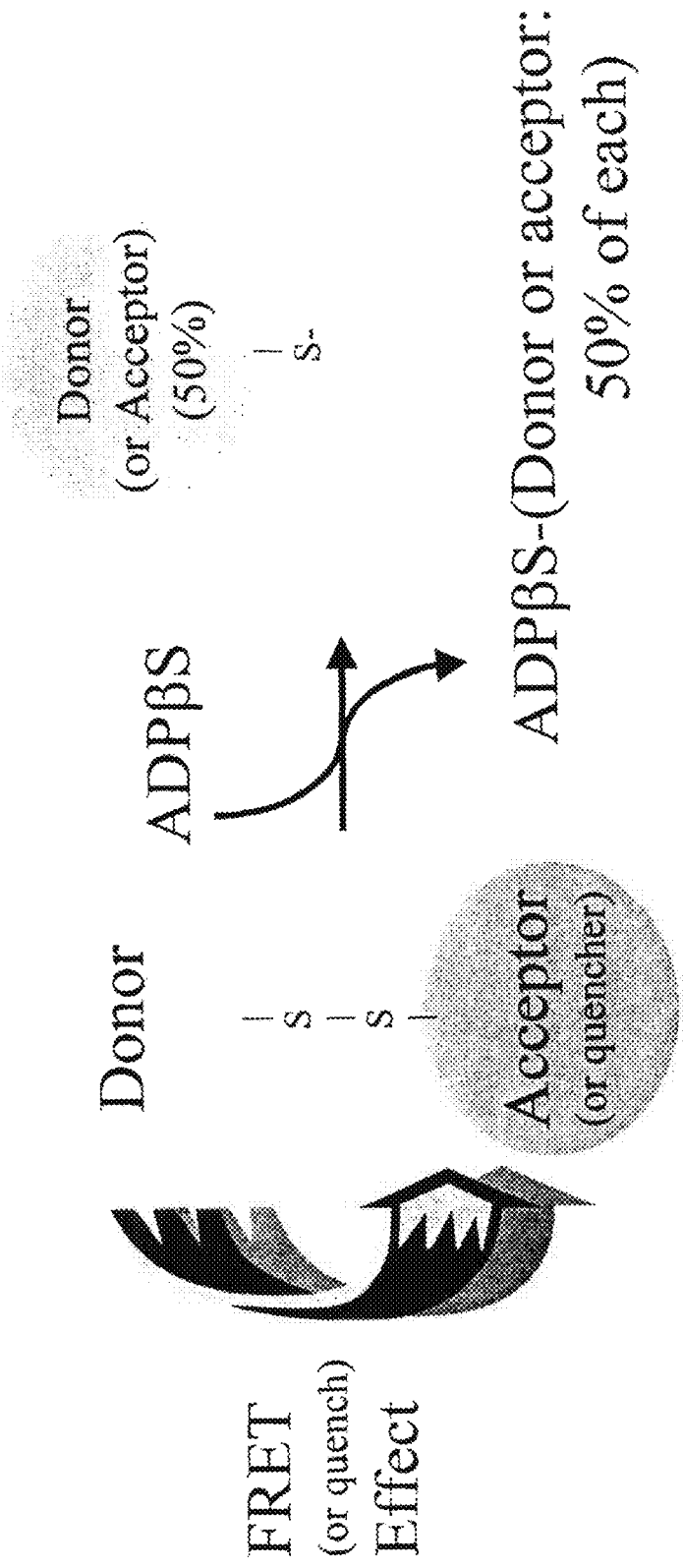
Figure 4. Schematic representation of kinase reaction utilizing FRET-based reagents for detection of ADPβS.

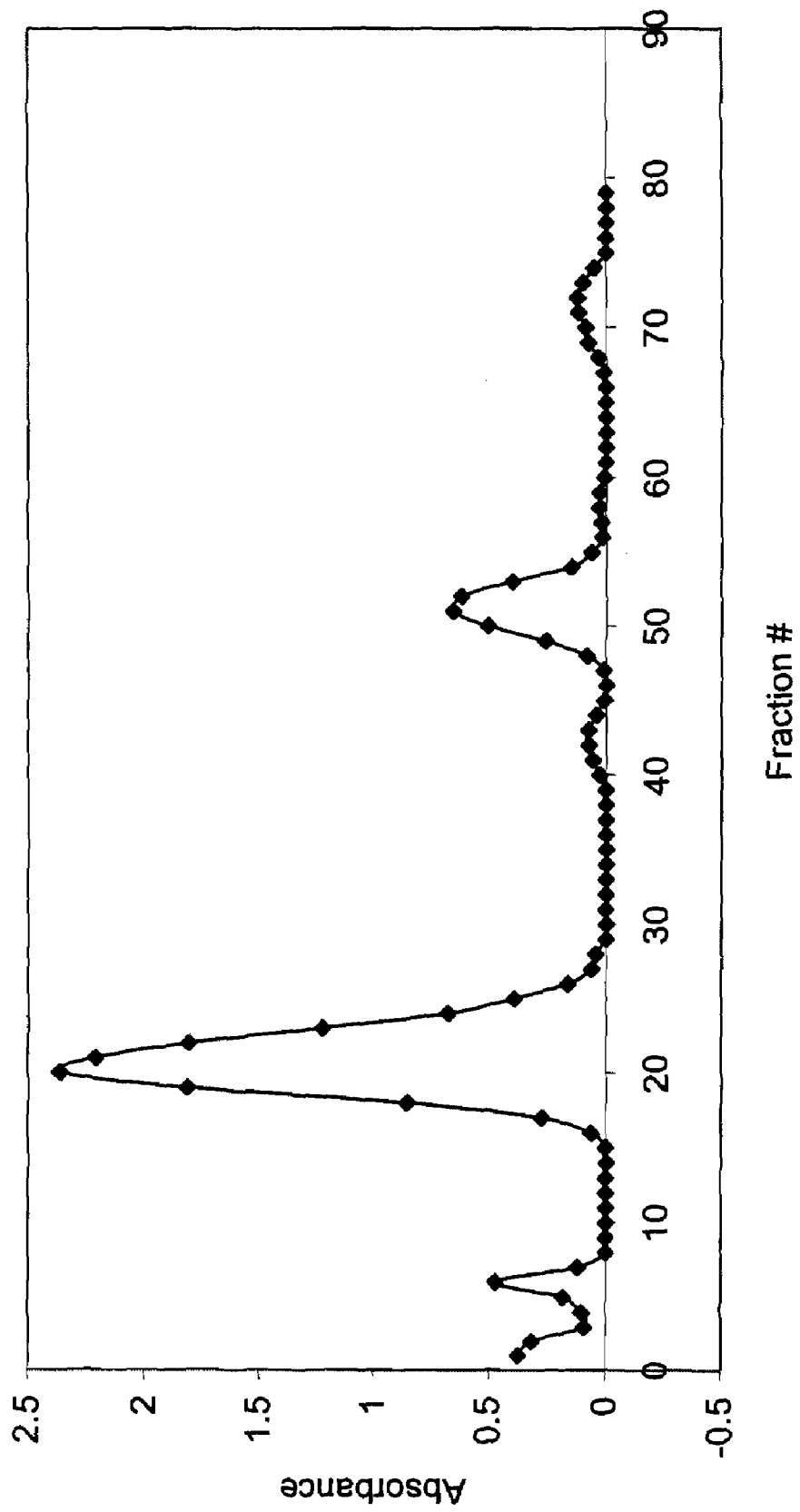
Figure 5. The elution profile for purification of ATPβS.

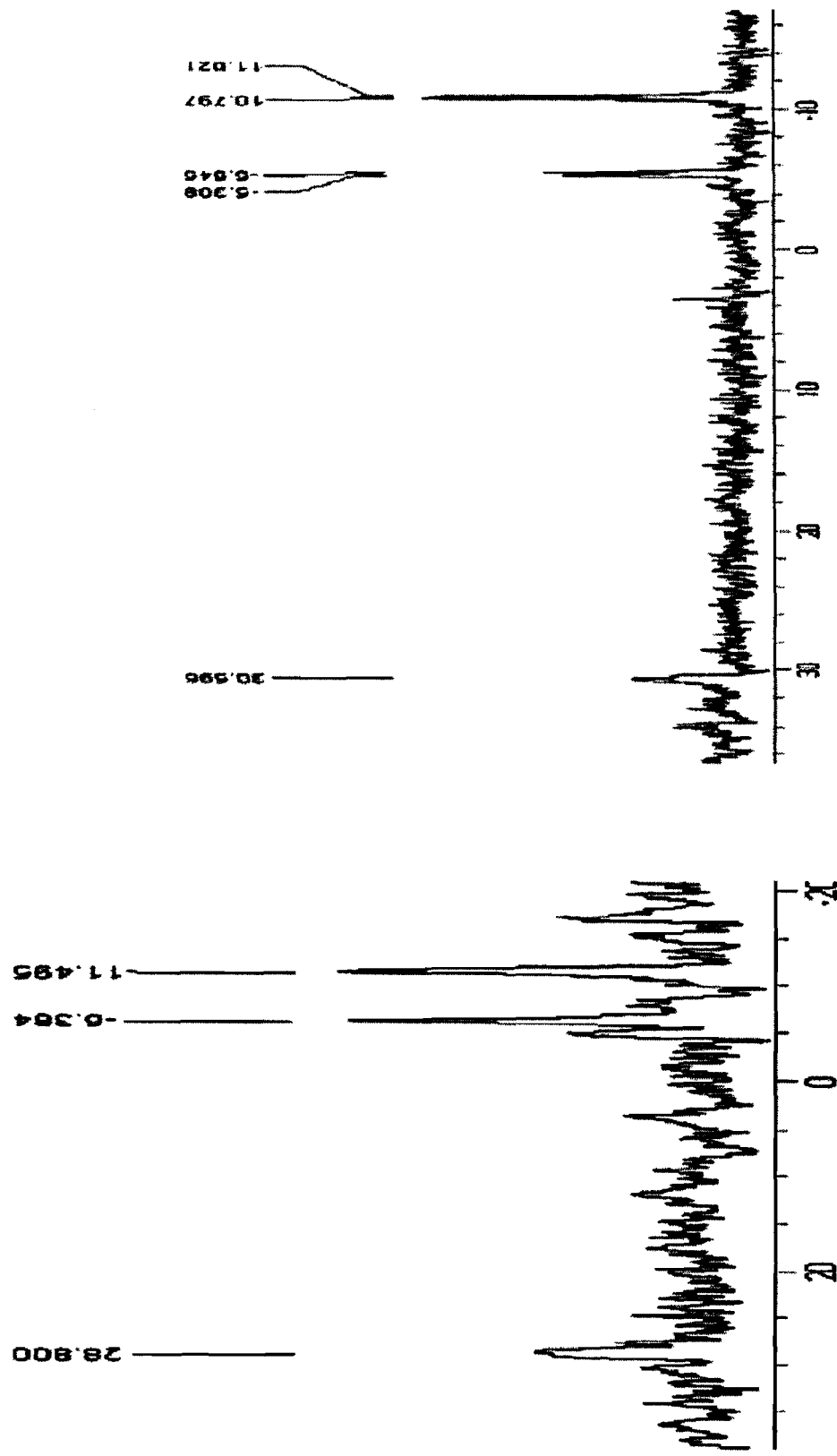
Figure 6. $^{31}$P NMR of ATPβS, (left) βR and (right) βS diastereomers

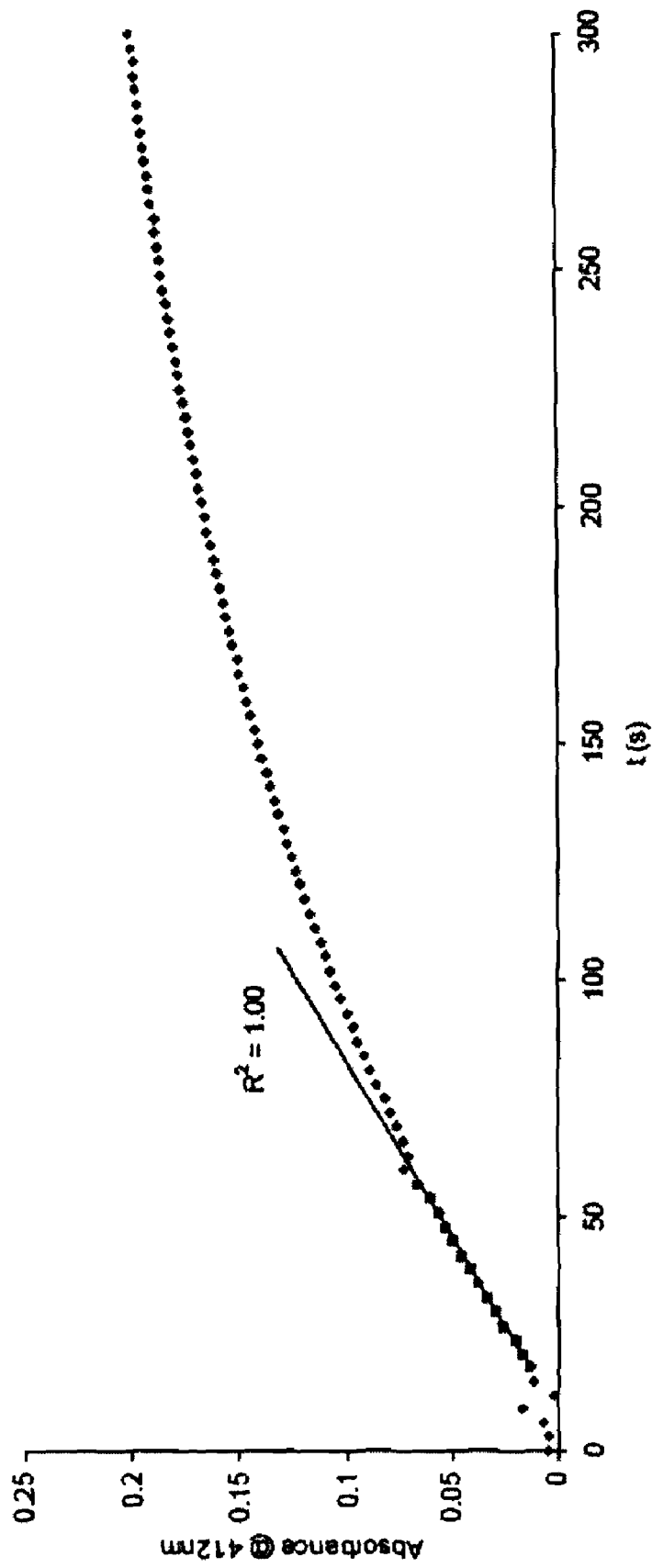
Figure 7. Typical progress curve for DTNB-coupled assay

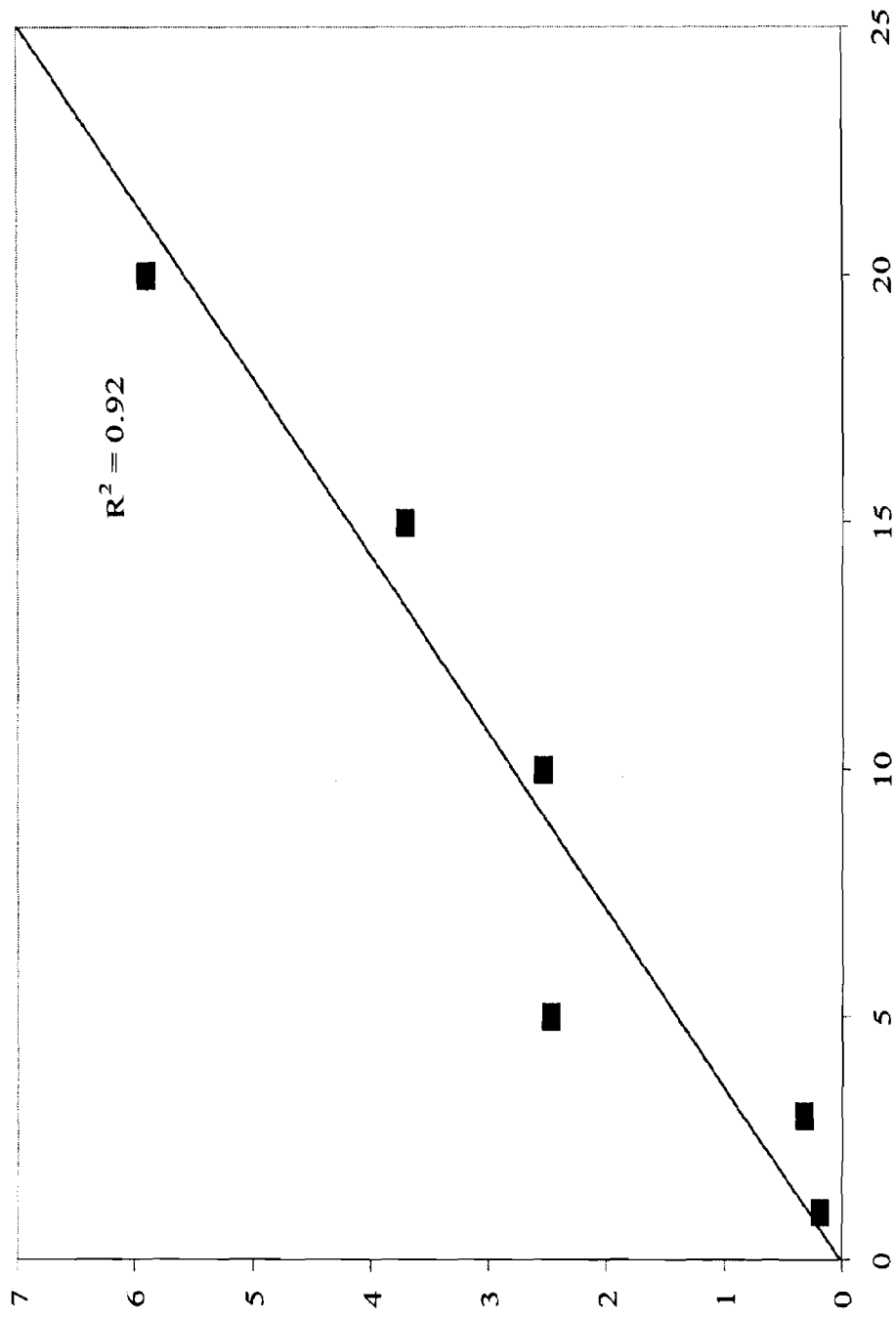
Figure 8. Validation curve for calcium-activated myosin hydrolysis of βS diastereomer of ATPβS in DTNB-coupled assay, initial rate (X100 μM/s) versus myosin concentration (U/ml)

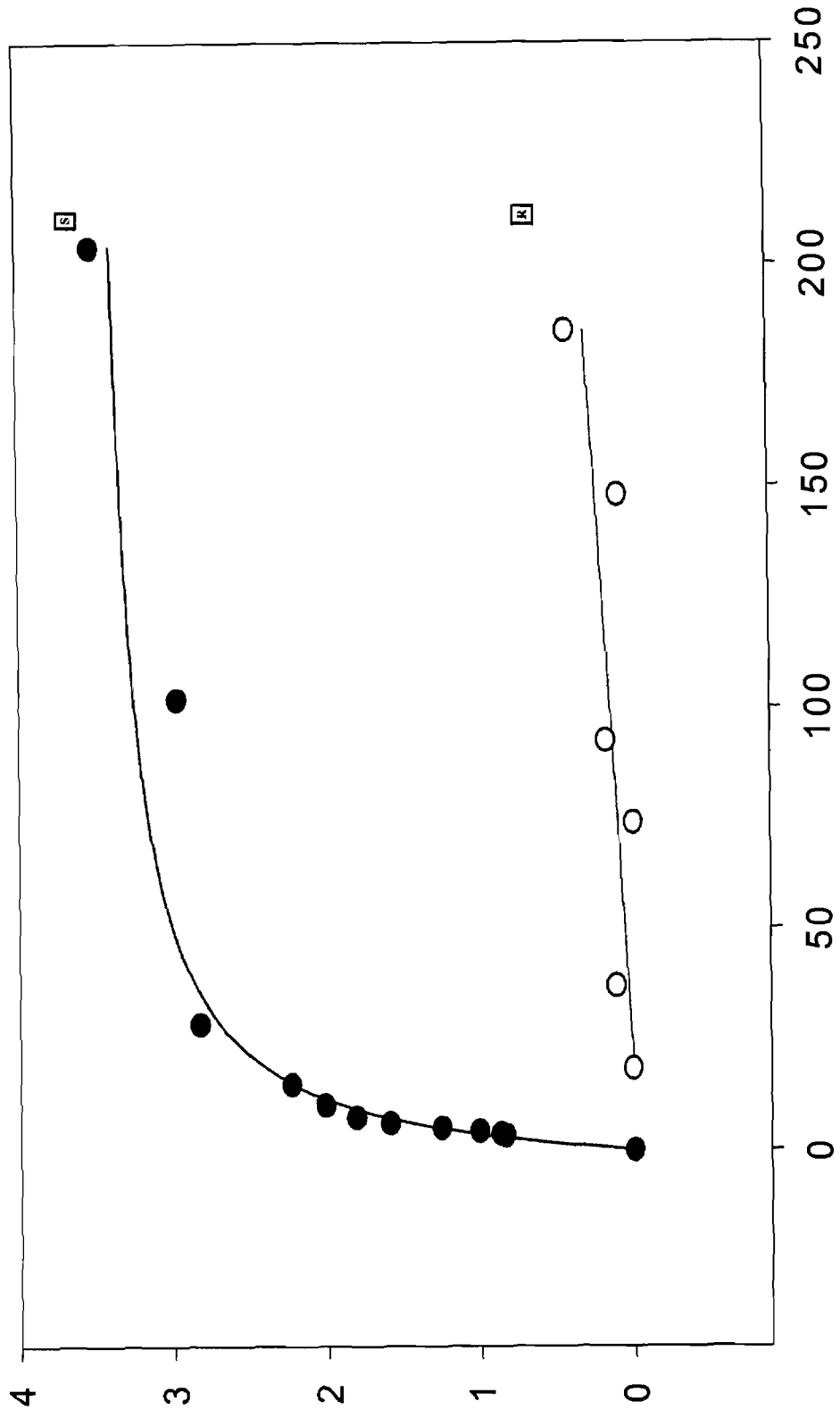
Figure 9. Variation of initial rate (X100 μM/s) versus concentration of ATPβS (μM) for both diastereomers in the DTNB-coupled assay

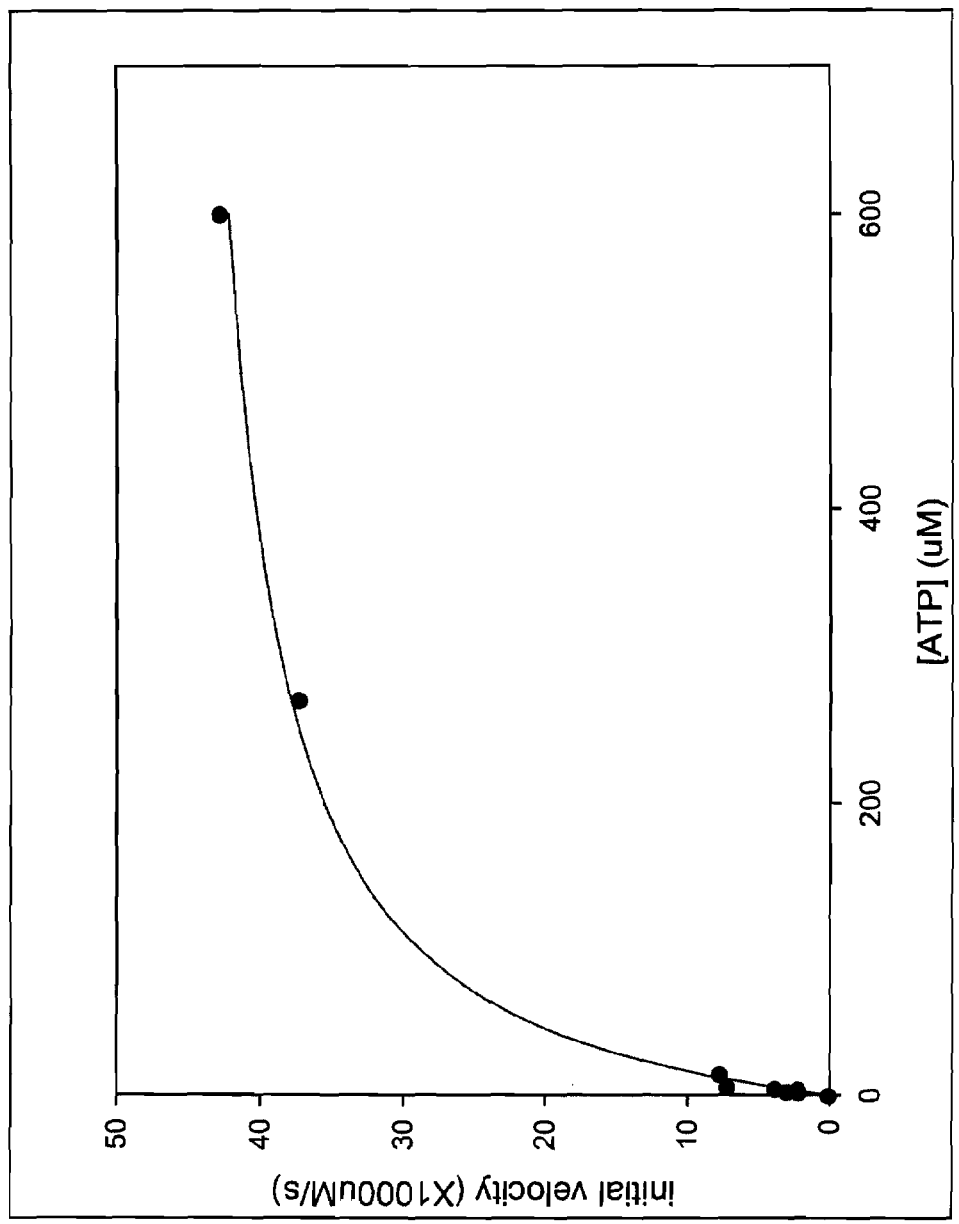
Figure 10. Variation of initial rate versus concentration of ATP for myosin using PK/LDH-coupled assay

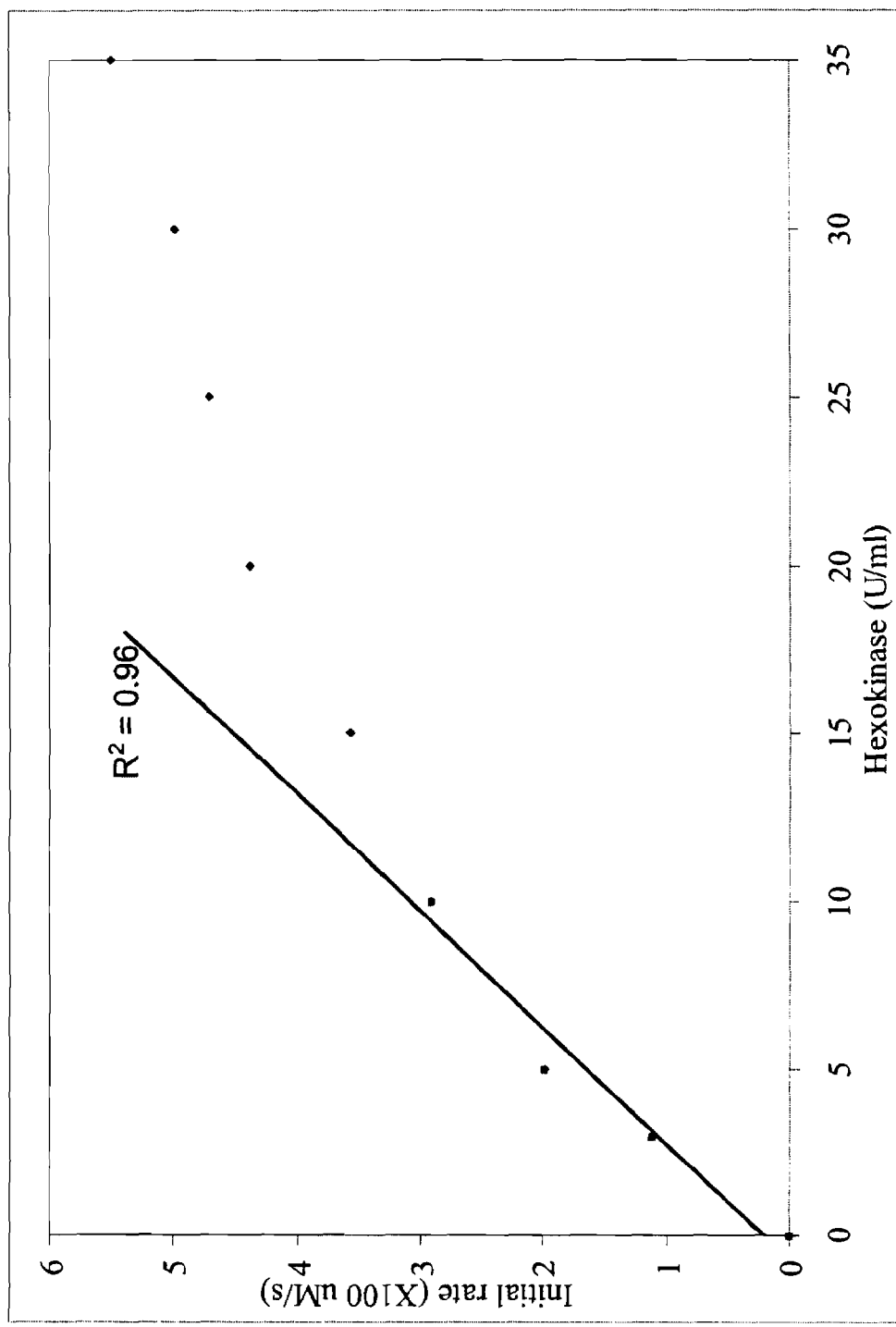
Figure 11. Validation curve for hexokinase using the βR diastereomer of ATPβS in DTNB-coupled assay

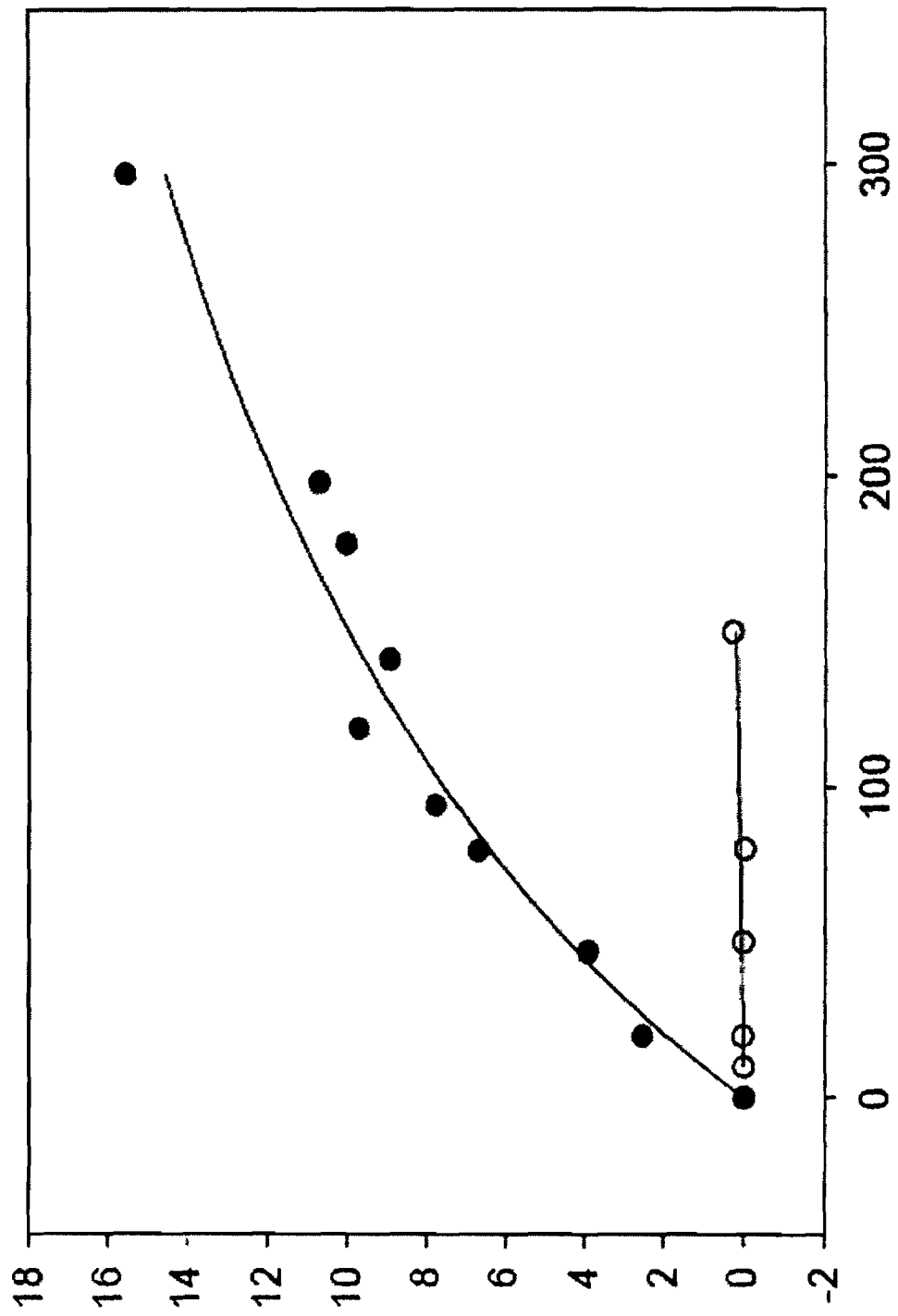
Figure 12. Variation of initial rate (X100 M/s) versus concentration (μM) for (βS) diastereomer (top curve) and (βR) diastereomer (bottom curve) of ATPβS in DTNB-coupled assay

| Enzyme | Phosphate Source | $K_M$ (μM) | $K_M$* | $V_{max}$ (μM/s) | $V_{max}$* |
|---|---|---|---|---|---|
| Myosin | ATPβS | 14.7±0.93 | 0.35 | 0.046±0.01 | 1.14 |
|  | ATP | 41.5±1.15 | 1.00 | 0.040±0.01 | 1.00 |
| Hexokinase | ATPβS | 3.69±0.11 | 0.06 | 5.32± 0.06 |  |
|  | ATP | 63.0±0.05 | 1.00 |  |  |

Figure 13: $K_M$* and $V_{max}$* for myosin and hexokinase for assays using ATPβS as a phosphate source relative to assays using ATP as a phosphate source

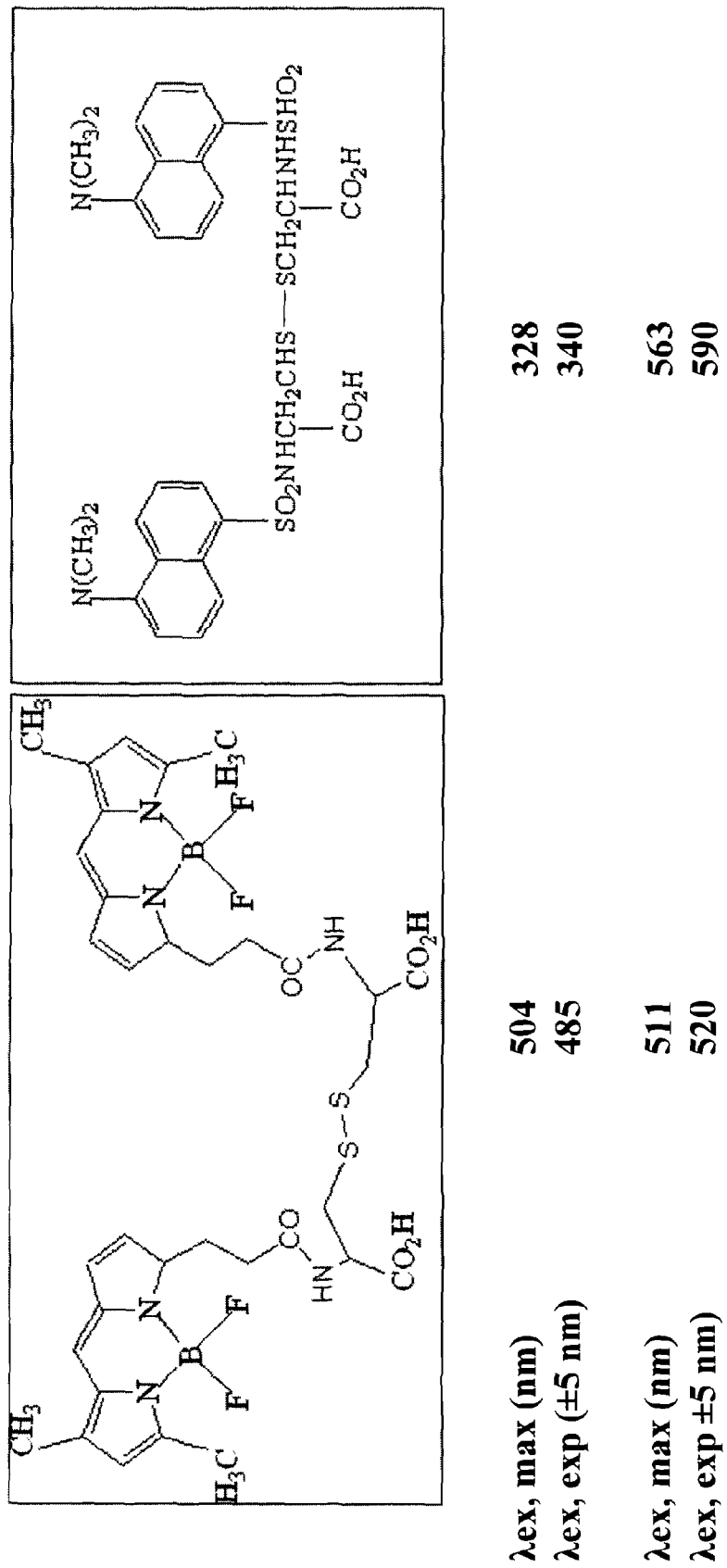
Figure 14: Dyes capable of internal quenching

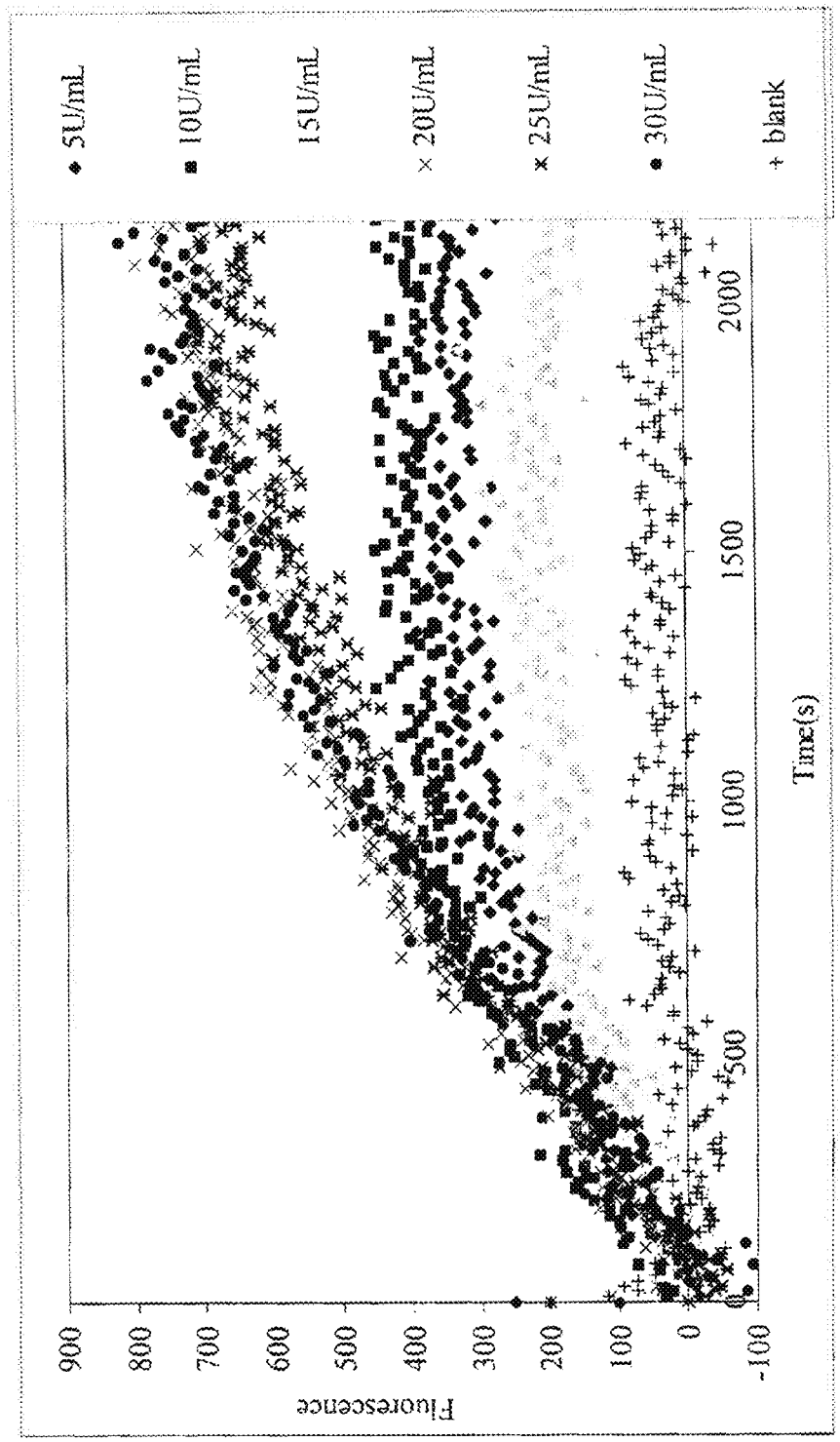
Figure 15. Hydrolysis of ATPβS by calcium-activated myosin as monitored by relief of fluorescence self-quenching of didansyl L-cystine

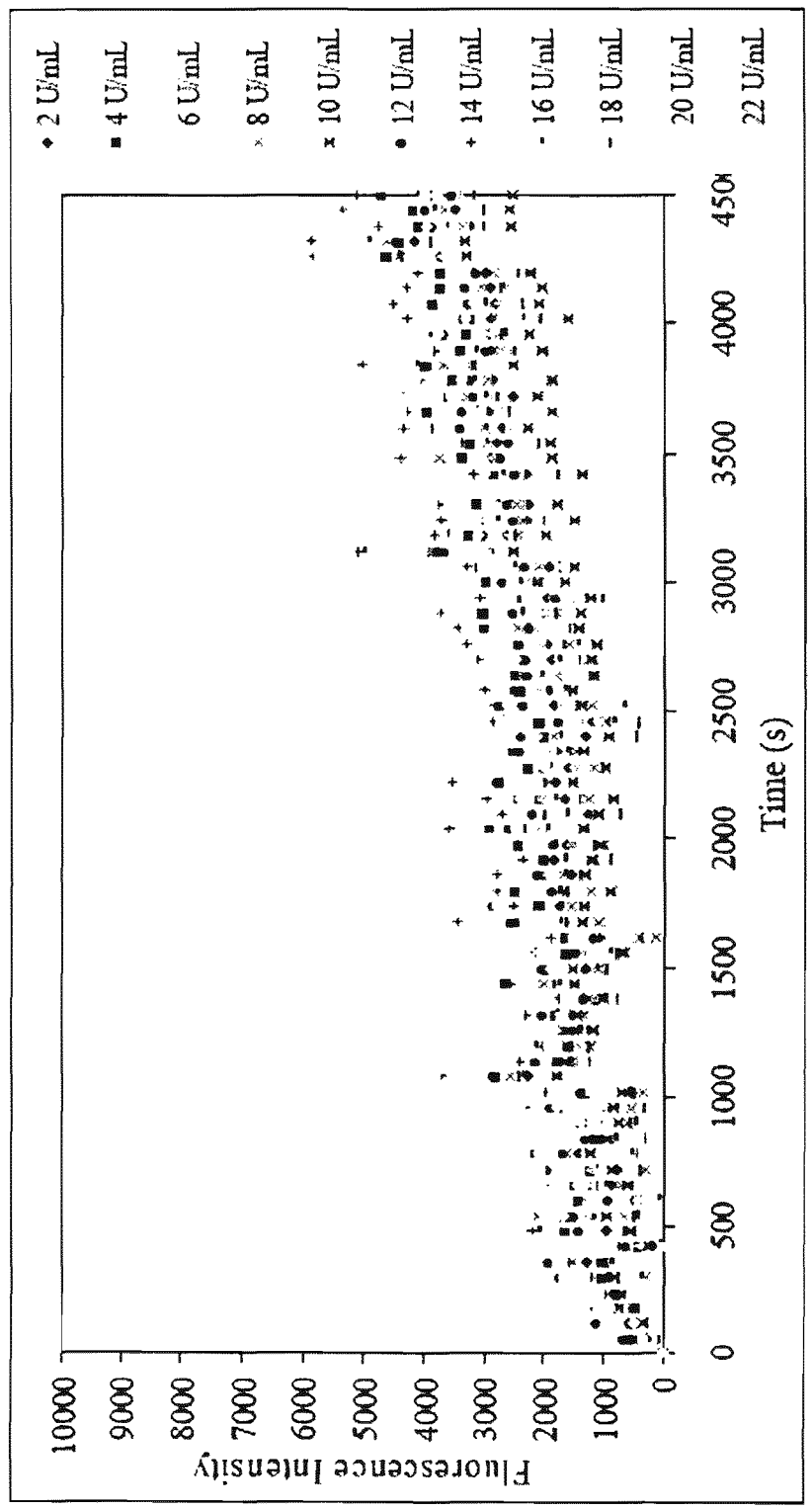
Figure 16. Production of ADPβS in hexokinase reaction monitored by relief of self-quenching of Bodipy FL L-cystine

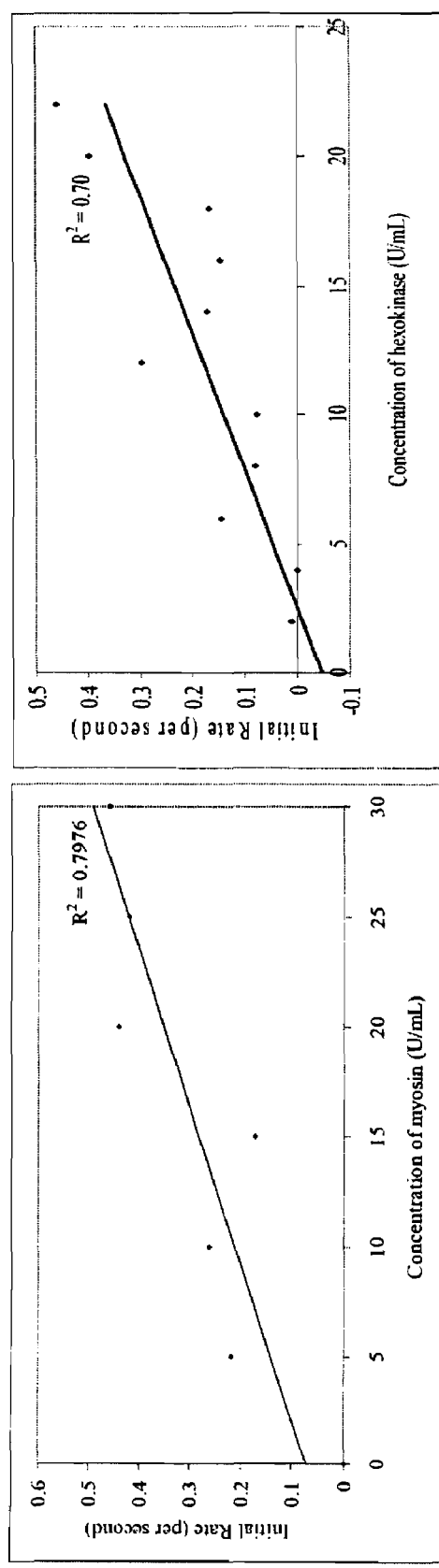
Figure 17. Validation curves for calcium-activated myosin (left) and hexokinase (right) corrected for background

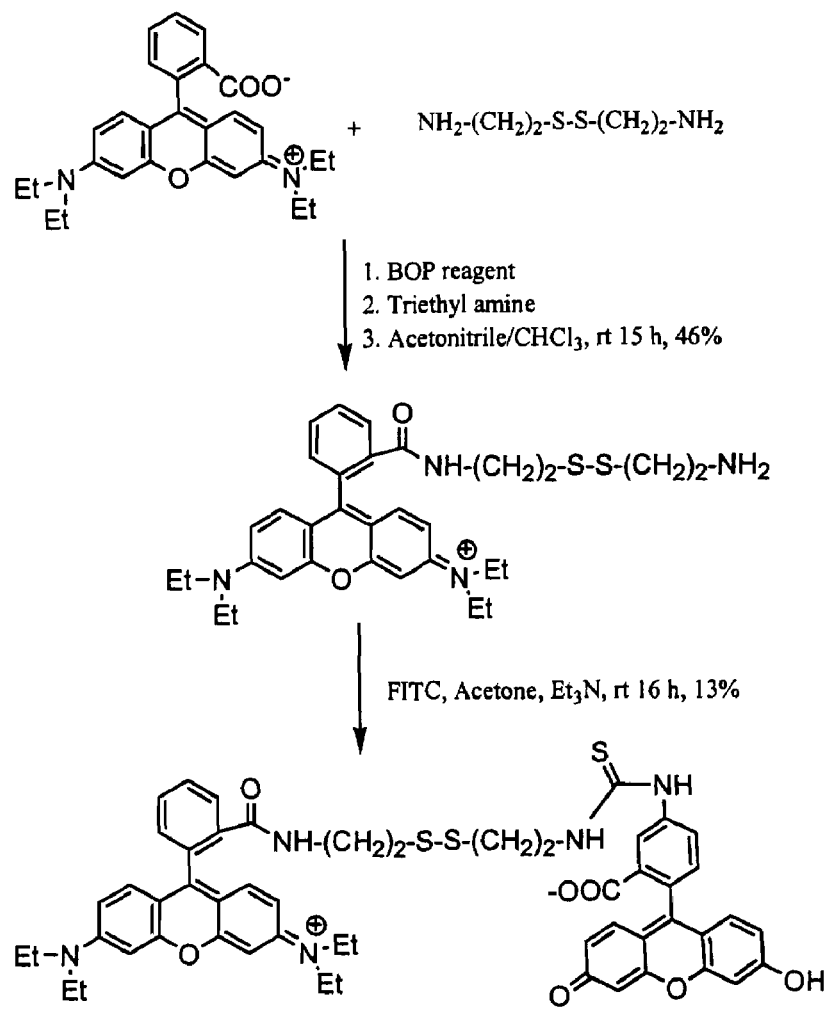
Figure 18. Synthesis of Dithio Reagent (Rhodamine-cystamine-S-S-cystamine-Fluorescein)

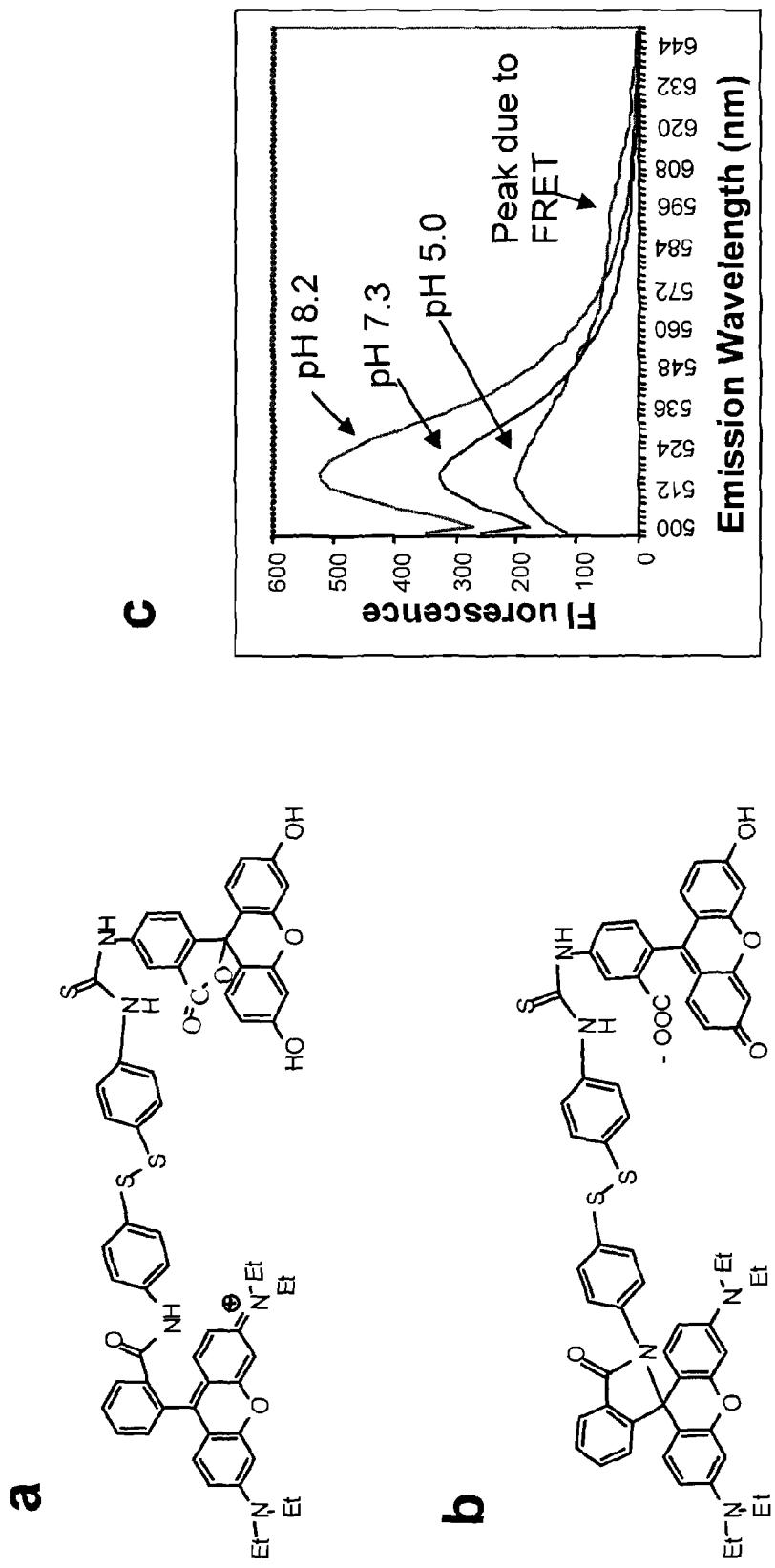
Figure 19. Fluorescense emission spectra (c) (excitation at 489 nm) of Rh-DAPS-FITC at acidic (a) and basic (b) pH

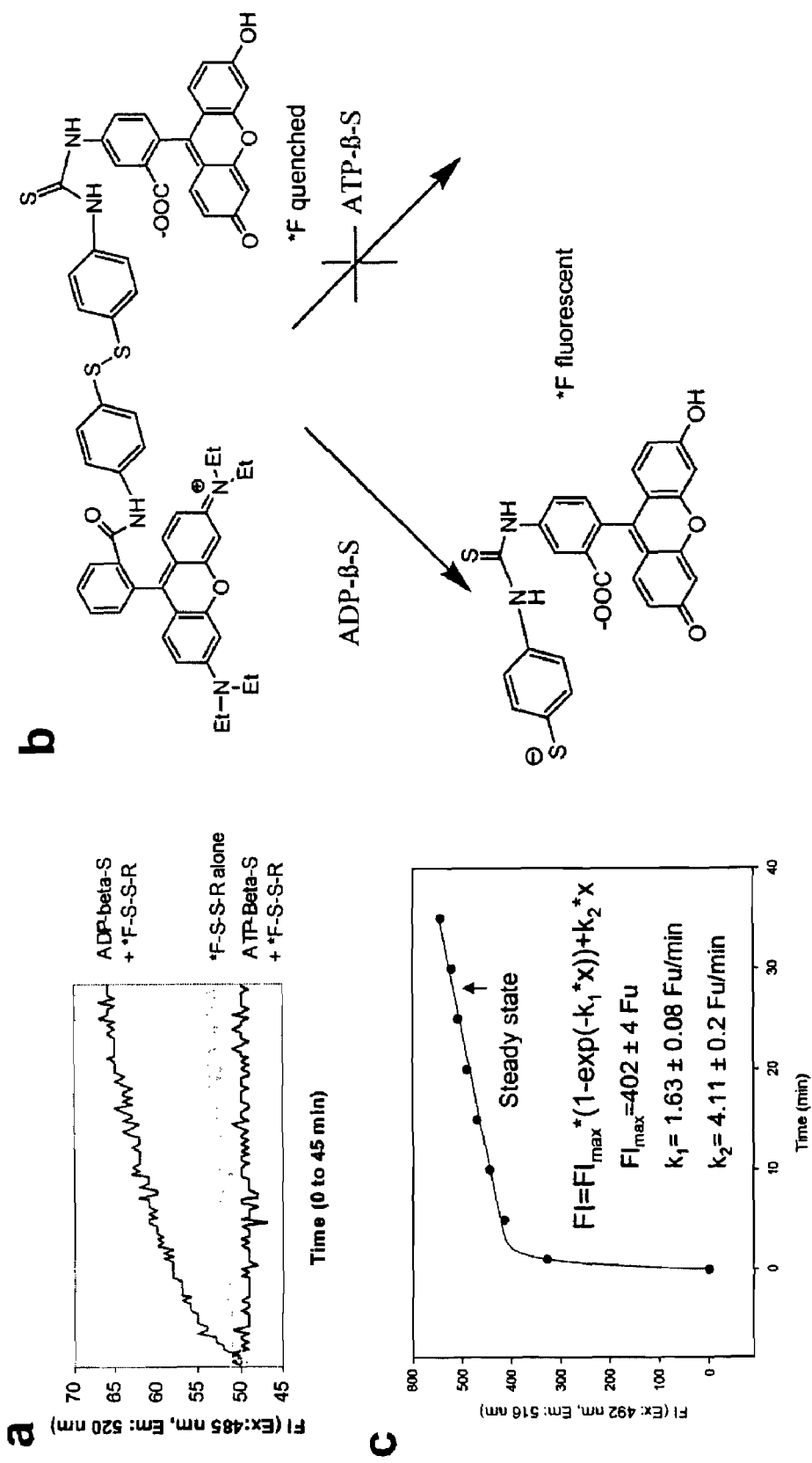
Figure 20. Selective detection of ADPβS versus ATPβS

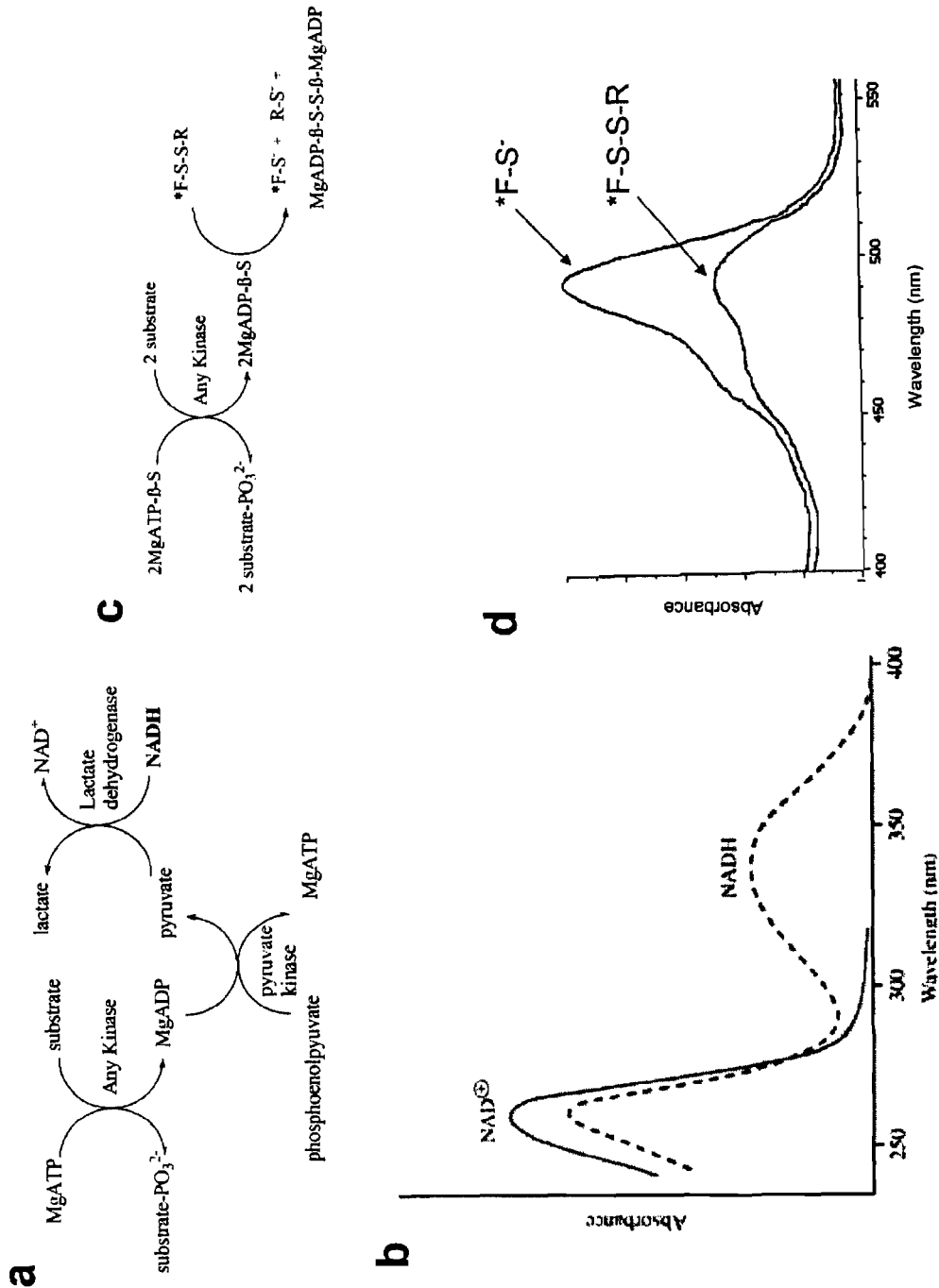
Figure 21. Common coupled kinase assay versus thiol-based F-DAPS-R coupled assay

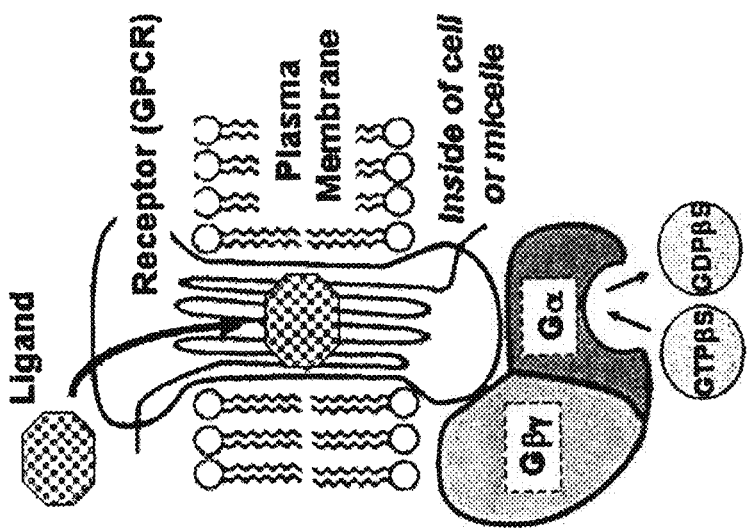
Figure 22. Model of a GPCR interacting with GTPβS

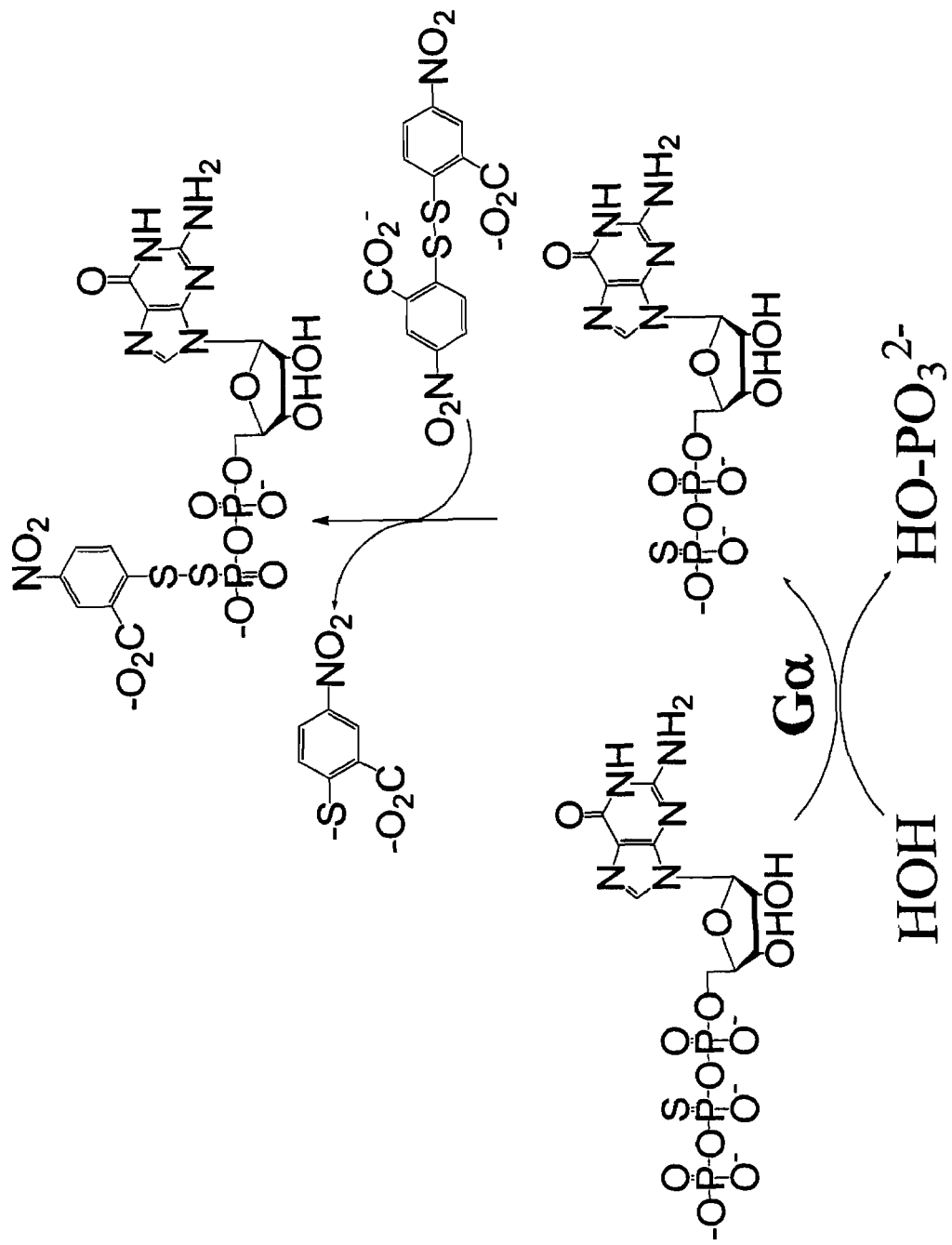
Figure 23. Dithio-coupled assay of the GTPase activity of Gα using DTNB

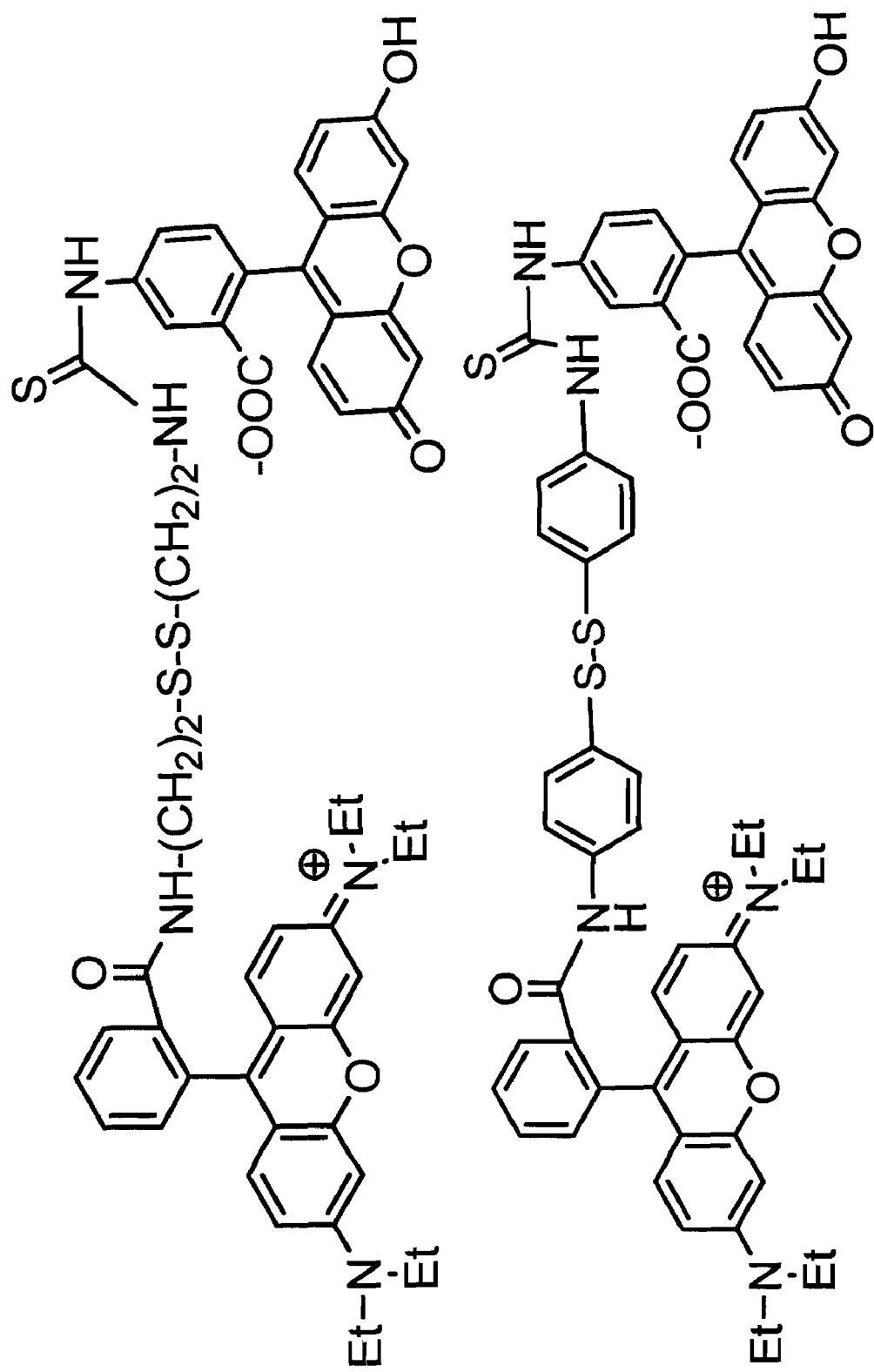
Figure 24. Exemplary "DSSA" reagents for use in dithio assay of the GTPase activity of Gα

_US 7,807,399 B2_

METHODS FOR DETECTING THIOL-CONTAINING NUCLEOTIDE DIPHOSPHATES WITH THIOL-REACTIVE FLUORESCENT REAGENTS

CROSS-REFERENCE TO RELATED APPLICATIONS

The present application is a continuation of U.S. application Ser. No. 11/512,832, filed on Aug. 30, 2006 now U.S. Pat. No. 7,585,643, which claims the benefit under 35 U.S.C. §119(e) of U.S. Provisional Application No. 60/715,090, filed on Sep. 8, 2005, the entire contents of which are incorporated herein by reference.

BACKGROUND

The disclosed methods relate to assays for detecting enzymatic activity. In particular, the disclosed methods relate to the use of thiol-reactive reagents for detecting enzyme activity.

Many enzymes are known to utilize phosphate as a signaling molecule. These include kinases, phosphatases, and enzymes associated with G-protein coupled receptor complexes (GPCRs). Protein kinases are one of the most widely studied classes of enzymes. They have been estimated to represent approximately 1.7% of the human genome, and over 500 kinases have been identified in the human "Kinome." Many protein kinases have been implicated in hyperproliferative diseases (e.g., cancer), and as such, interest is focused on understanding the function of these enzymes and on identifying modulators of their activity. With the initial identification of kinase-targeted drugs, there has been renewed interest in pursuing protein kinases as drug targets. A number of kinase inhibitors are in various stages of clinical trials. As such, there is tremendous interest in the broad study of ligand-enzyme interactions with respect to kinases, and there is a general need for better tools for studying these interactions.

Commonly used kinase assays are either fixed-time (i.e., assaying data at a single data point) or continuous (i.e., assaying data at multiple data points). Fixed time kinase assays typically employ indirect detection mechanisms, such as monitoring binding of a phosphorylated product to an immobilized metal ion or antibody. Such assays are not ideal, in that they use multiple reagents and employ indirect measurements. Furthermore, typical fixed-time kinase assays require the presence of the kinase's substrate that is phosphorylated. Another disadvantage of all fixed time assays is that because they provide single time-point measurements, they can produce artifactual measurements that could have been diagnosed by monitoring a continuous rate of reaction over the course of the assay.

Continuous assays provide multiple time point measurement to define an enzymatic rate. Commonly, continuous assays involve an enzyme-coupling reaction. In one common enzyme-coupling system, the kinase reaction is coupled to a pyruvate kinase/lactate dehydrogenase reaction ("PK/LDH") and one of the ultimate reaction products of the PK/LDH reaction is used to monitor kinase activity (i.e., NAD$^+$). In this system, the assayed kinase converts ATP to ADP. Pyruvate kinase then utilizes ADP to generate pyruvate from phosphoenol pyruvate. Finally, lactate dehydrogenase converts pyruvate to lactate and concurrently converts NADH to NAD$^+$. As such, the decrease in concentration of NADH may be monitored over time based on the absorbance of NADH at $\lambda$=340 nm and correlated with kinase activity. This system may not be ideal in that it involves three coupled reactions. Further, NADH has a low extinction coefficient ($\epsilon_{340nm}$=6.22 mM$^{-1}$cm$^{-1}$). In addition, the PK/LDH assay involves monitoring a decrease in signal rather than an increase in signal, which limits the dynamic range and makes the assay more difficult to optimize.

Therefore, although kinase assays are presently available, there is a need for a continuous assay that monitors an increasing signal, and permits assay of kinases even when their natural substrate is unknown, as is common in a functional genomics project. Assays that involve direct detection of ADP, or an analog thereof, are potentially universal assays for kinases, and would not require that the natural substrate be present, because most kinases will slowly hydrolyze ATP even in the absence of their natural substrate (i.e., commonly called the "ATPase" or hydrolysis reaction).

GPCRs (G-protein coupled receptors) play an important role in communicating signals from the outside to the inside of cells. The external signal for these receptors may include light, hormones, growth factors, and various ligands that bind to the GPCR. An agonist signal activates exchange of GTP for GDP bound to the G$\alpha$ subunit of the GPCR-complex, which stimulates release of the G$\beta\gamma$ subunits, permitting downstream activation of other proteins. This activated state is only transient though, because the bound GTP is slowly hydrolyzed to GDP by the intrinsic GTPase activity of G$\alpha$, and the G$\alpha$/GDP complex then rebinds to the G$\beta\gamma$ subunits to reform the inactive state of the GPCR. Furthermore, there are regulators of G-protein signaling (RGS) that can act as GTPase activating proteins (GAPs), and activate the GTPase activity of the G$\alpha$ subunit. Given the important role of GPCRs in cell biology, as well as their prevalence as drug targets, there is a need for improved assays of GPCR activity, and for methods to quantitate the effect of antagonists—which could serve as potential drug leads. For example, Seifert et al. (J. of Pharmacology and Experimental Therapeutics (2003) 305, 1104-1115) reported the screening and identification of antagonists of the histamine H1 receptor (a GPCR, termed H$_1$R), which could lead to treatments for allergic diseases. The Seifert et al. assay involved monitoring GTPase activity of the G$\alpha$ subunit of H$_1$R by observing the release of radioactive phosphate from [$\gamma$-$^{32}$P]GTP, analogous to commonly used kinase assays using [$\gamma$-$^{32}$P]-ATP. There is a need for better assays that may be used to monitor the activation state of GPCRs including continuous assays.

SUMMARY

Disclosed are methods that utilize thiol-reactive reagents for detecting enzyme activity. Generally, the methods relate to detecting thiol-containing nucleotide diphosphates in a reaction mixture. The methods may be used in continuous assays for measuring enzyme activity.

The methods may be useful for detecting enzyme activity related to conversion of ATP (or analogs of ATP) to ADP (or a respective analog). In particular, the methods disclosed herein are useful for detecting enzyme activity related to conversion of the ATP analog ATP$\beta$S to ADP$\beta$S or GTP$\beta$S to GDP$\beta$S. The methods typically involve detecting a substituted nucleotide diphosphate in which the beta-oxygen atom is replaced with a sulfur atom (e.g., ADP$\beta$S and GDP$\beta$S).

The methods may be useful for detecting the activity of any enzyme that converts ATP (or an ATP analog) to ADP (or an ADP analog). For example, the methods may be useful for detecting an enzyme that converts ATP$\beta$S to ADP$\beta$S or GTP$\beta$S to GDP$\beta$S. In particular, the method may be useful for detecting kinase activity and/or phosphatase activity (e.g., ATPase and GTPase activity). Kinase activity may include ATPase activity (e.g. where water is a substrate for phosphate addition by the kinase). The methods may be useful for identifying a modulator of enzyme activity, such as a kinase inhibitor, an ATPase inhibitor, or a GTPase inhibitor. In some embodiments, the methods may be used to detect GTPase activity, such as GTPase activity associated with GPCRs. The methods may be used to identify modulators of GPCRs such as receptor agonists and antagonists.

The methods for detecting enzyme activity typically includes reacting a reaction mixture that includes a sample to be tested for enzyme activity. Where the enzyme utilizes a substrate, optionally, the reaction mixture may include the substrate for the enzyme. Additionally, the reaction mixture typically includes a substituted nucleotide triphosphate in which the beta-oxygen atom is replaced by a sulfur atom (e.g., ATPβS or GTPβS), and a reagent for detecting a substituted nucleotide diphosphate in which the beta-oxygen atom is replaced by a sulfur atom (e.g., ADPβS or GDPβS). Typically, the reagent has at least one functional group that reacts with a thiol group of ADPβS or GDPβS and forms at least one reaction product that may be used to detect ADPβS or GDPβS. Enzyme activity may be detected by detecting the at least one reaction product. The reagent may include a fluorescent dithio reagent. Optionally, the reaction mixture include at least one divalent cation.

The methods may be useful for detecting kinase activity. In some embodiments, the method for detecting kinase activity may comprise reacting a reaction mixture. The reaction mixture typically includes a sample to be tested for kinase activity. Typically, the reaction mixture includes a substituted nucleotide triphosphate in which the beta-oxygen atom is replaced by a sulfur atom (e.g., ATPβS or GTPβS) and a reagent for detecting a substituted nucleotide diphosphate in which the beta-oxygen atom is replaced by a sulfur atom (e.g., ADPβS or GDPβS). Typically, the reagent has at least one functional group that reacts with a thiol group of ADPβS or GDPβS and forms at least one reaction product that may be used to detect ADPβS or GDPβS. Optionally, the reaction mixture may include a substrate for the kinase and at least one divalent cation. Kinase activity may be detected by detecting the at least one reaction product. The reagent may include a fluorescent dithio reagent.

The method may be useful for testing a sample for enzyme activity (e.g., kinase activity, ATPase activity, or GTPase activity). The method may be performed by reacting a reaction mixture that includes: a sample to be tested for enzyme activity; a substituted nucleotide triphosphate in which the beta-oxygen atom is replaced by a sulfur atom (e.g., ATPβS or GTPβS); and a reagent for detecting a substituted nucleotide diphosphate in which the beta-oxygen atom is replaced by a sulfur atom (e.g., ADPβS or GDPβS). Optionally, the reagent may be added to the reaction mixture subsequently to adding the enzyme and the substituted nucleotide triphosphate. Optionally, the reaction mixture may include a substrate for the enzyme and at least one divalent cation. In some embodiments, the reagent has at least one functional group that reacts with the thiol group of ADPβS or GDPβS and forms at least one reaction product that may be used to detect ADPβS or GDPβS. Enzyme activity may be detected by detecting the at least one reaction product.

The methods may be used to identify agonists and antagonists for GPCRs. In some embodiments, the methods include contacting a GPCR-complex with a test agent (e.g., a test compound or physical stimulus such as light of a selected wavelength) and then detecting GTPase activity or the lack thereof. A GPCR-complex may include the GPCR and G-protein (and optionally components that form natural or artificial membranes such as amphiphilic fatty acids). The G-protein may include one or more of an alpha subunit (Gα), beta subunit (Gβ), and gamma subunit (Gγ). Typically, the G-protein includes the Gα subunit. Detecting GTPase activity may include detecting GTPase activity associated with the Gα subunit of the G-protein. In some embodiments, after the GPCR-complex is contacted with the test compound, at least the Gα subunit of the GPCR-complex is reacted with GTPβS and a reagent that has at least one functional group that reacts with a thiol group of GDPβS and forms at least one reaction product that may be used to detect GDPβS. The agonist or antagonist may be identified by detecting the at least one reaction product. The reagent may include a fluorescent dithio reagent. Optionally, the methods for identifying agonists and antagonists for GPCRs may be performed in a reaction mixture that includes additional components such as components that form natural or artificial membranes (e.g., amphiphilic fatty acids), detergents (such as non-ionic detergents like Triton® X-100 detergent or ionic detergents like sodium dodecyl (lauryl) sulfate (SDS)), and divalent cations.

The methods may be useful for performing continuous assays (i.e., real-time assays), in which detecting the at least one reaction product occurs contemporaneously as the reaction product is formed in the reaction mixture. The reaction product may include a label useful for performing continuous assays (i.e., real-time assays).

The divalent cation typically binds to ATP or an analog thereof such as ATPβS or GTPβS. The divalent cation may include a divalent metal ion. Suitable divalent metal ions may include $Mg^{2+}$, $Cd^{2+}$, $Co^{2+}$, $Cr^{2+}$, $Mn^{2+}$ and mixtures thereof. Desirably, the reaction mixture includes $Mg^{2+}$ as a divalent cation.

The at least one reaction product typically includes a label. The label may include a fluorophore, a chromophore, radioisotope, or a combination thereof. Fluorophores may include any useful fluorophore as known in the art. In some embodiments, the fluorophore may include fluorescein, rhodamine, pyrromethene boron difluoride, a dansyl group, coumarin, or combinations thereof. Chromophores may include any useful chromophore as known in the art. In some embodiments, the chromophore may include 5-mercapto-2-nitrobenzoic acid. Chromophores may include fluorophores. Suitable radioisotopes may include any useful radioisotope as known in the art. In some embodiments, the radioisotope may include $^3H$, $^{14}C$, $^{35}S$, $^{32}P$, $^{125}I$, and $^{131}I$.

The reagent typically will have a change in absorbance and/or emission at a given wavelength, upon reduction of its dithio group. The reagent may have a formula $R^1$—S—S—$R^2$. In some embodiments, $R^1$ and $R^2$ are the same or different, and at least one of $R^1$ and $R^2$ includes a label. The at least one reaction product may have a formula selected from the group consisting of ADPβS-S—$R^1$, ADPβS-S—$R^2$, GDPβS-S—$R^1$, GDPβS-S—$R^2$, $R^1$—S—H, $R^2$—S—H, and salts thereof. Salts thereof may include ionized forms of the at least one reaction product (e.g., $R^1$—$S^-$, $R^2$—$S^-$).

Suitable reagents for performing the disclosed methods are described in U.S. provisional application No. 60/715,114, filed on Sep. 8, 2005; Pullela et al., "Fluorescence-based detection of thiols in vitro and in vivo using dithiol probes," ANAL. BIOCHEM. (2006) 352(2):265-73; and in Chiku et al., "A Dithio Coupled Assay and ATPase assay," JOURNAL OF BIOMOLECULAR SCREENING 11(X); (2006) (accepted for publication Jun. 21, 2006, not yet published); which are incorporated by reference herein in their entireties. The reagent may have a formula $R^1$—S—S—$R^2$, in which $R^1$ may include a first fluorophore and $R^2$ may include a second fluorophore. In some embodiments, the first fluorophore may have an emission spectrum and the second fluorophore may have an absorption spectrum, such that the emission spectrum and the absorption spectrum overlap. The emission spectrum and the absorption spectrum may overlap by at least about 10%, and desirably the emission spectrum and the absorption spectrum may overlap by at least about 20%, 30%, 40%, or 50%. In some embodiments, the first fluorophore and the second fluorophore are present in the reagent at a distance of about 10-100 angstroms, and preferably 25-75 angstroms or more preferably about 30-70 angstroms. In further embodiments, the first fluorophore and the second fluorophore are present in the reagent at a distance of about 3-100 angstroms, and preferably 3-75 angstroms or more preferably about 3-50 angstroms.

The reagent may have a formula $R^1$—S—S—$R^2$, in which $R^1$ and $R^2$ comprise identical fluorophores. In some embodiments, detecting the at least one reaction product may include observing a decrease in self-quenching. In some embodiments, detecting the at least one reaction product may include observing a decrease or increase in fluorescence polarization or depolarization (i.e., a change in polarization).

The reagent may have a formula $R^1$—S—S—$R^2$, in which $R^1$ may include a first fluorophore and $R^2$ may include a second fluorophore or non-fluorophore. In some embodiments, detecting the at least one reaction product may include observing dequenching of the first fluorophore. In some embodiments, detecting the at least one reaction product may include observing a decrease in sensitized fluorescence of the second fluorophore. The second fluorophore or non-fluorophore may have a molecular weight that is at least about 2× the molecular weight of the first fluorophore, (preferably at least about 4× the molecular weight of the first fluorophore), and detecting the at least one reaction product may include observing a decrease or increase in fluorescence polarization (e.g., detecting a decrease or increase in fluorescence polarization of the first fluorophore).

The reagent may have a formula $R^1$—S—S—$R^2$, in which $R^1$ may include a first fluorophore having an emission spectrum and $R^2$ may include a non-fluorophore having an absorption spectrum such that the emission spectrum and absorption spectrum overlap. In some embodiments, the fluorophore and the non-fluorophore are present in the reagent at a distance of about 10-100 angstroms, and preferably 25-75 angstroms or more preferably about 30-70 angstroms. In further embodiments, the fluorophore and the non-fluorophore are present in the reagent at a distance of about 3-100 angstroms, and preferably 3-75 angstroms or more preferably about 3-50 angstroms. In some embodiments, detecting the at least one reaction product may include observing dequenching of the fluorophore. The non-fluorophore may include a chromophore.

The reagent may have a formula $R^1$—S—S—$R^2$, in which $R^1$ may include a fluorophore and $R^2$ may include a non-fluorophore. The non-fluorophore may quench the fluorophore.

The reagent may have a formula $R^1$—S—S—$R^2$, in which $R^1$ may include a fluorophore and $R^2$ may include a non-fluorophore. The non-fluorophore may have a molecular weight that is at least about 2× the molecular weight of the fluorophore, (preferably at least about 4× the molecular weight of the fluorophore), and detecting the at least one reaction product may include observing a change in fluorescence polarization (e.g., a decrease in fluorescence polarization of the fluorophore).

The reagent may have a formula $R^1$—S—S—$R^2$, in which one of $R^1$ and $R^2$ includes a radiolabel and the other of $R^1$ and $R^2$ includes a scintillant. A radiolabel may include a radioisotope. In some embodiments, detecting the at least one reaction product may include performing a scintillation proximity assay.

In some embodiments, the reagent may have the formula $R^1$-$A^1$-S—S-$A^2$-$R^2$ in which $R^1$ and $R^2$ are the same or different; at least one of $R^1$ and $R^2$ includes a label; and at least one of $A^1$ and $A^2$ includes an aryl group. In some embodiments, the aryl group may be selected from a phenyl group and a pyridinyl group.

The reaction mixture may include a reducing agent, for example, a reducing agent that reduces dithio groups (i.e., a dithio-reducing agent). Desirably, the dithio-reducing agent reacts with dithio groups present in proteins (e.g., dicysteine dithio groups), but is less reactive with dithio groups present in the reagent used for detecting ADPβS or GDPβS. Dithio-reducing agents may include phosphine-containing agents, dithiothreitol ("DTT"), beta-mercaptoethanol, and mixtures thereof. Desirably, the dithio-reducing agent includes a phosphine-containing agent. In one embodiment, the dithio-reducing agent includes a phosphine having the formula:

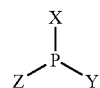

in which X, Y, and Z, independently are selected from the group consisting of hydrogen, alkyl, alkenyl, alkynyl, aryl, and carboxyalkyl. The dithio-reducing agent may include a phosphine such as Tris(2-carboxyethyl)phosphine ("TCEP").

The reaction mixture typically includes an analog of ATP, such as a substituted nucleotide triphosphate in which the beta-oxygen atom is replaced by a sulfur atom (e.g., ATPβS or GTPβS). The substituted nucleotide triphosphate (e.g., ATPβS or GTPβS) may comprise a mixture of diastereomers, and the substituted nucleotide triphosphate may be enriched in one or more diastereomers. For example, in some embodiments, the substituted nucleotide triphosphate is ATPβS (or GTPβS) having an ATPβS (βS) diastereomer content (or GTPβS (βS) diastereomer content) of at least about 80%, preferably at least about 90% or more preferably at least about 95%. In some embodiments, the substituted nucleotide triphosphate is ATPβS (or GTPβS) having an ATPβS (βR) diastereomer content (or GTPβS (βR) diastereomer content) of at least about 80%, preferably at least about 90% or more preferably at least about 95%.

The reaction mixture typically includes a suitable substrate. In some embodiments, water may function as a suitable substrate. In some embodiments, the substrate is selected from the group consisting of a polypeptide, a carbohydrate, a nucleotide, a fatty acid, and mixtures thereof. Polypeptides may include polypeptides that include at least one of a serine residue, a threonine residue, a tyrosine residue, and a histidine residue.

Also disclosed is a method for identifying a test substance that inhibits enzyme activity (e.g., kinase activity, ATPase activity, and GTPases) in a reaction mixture as described herein. Typically, the reaction mixture may include the enzyme; optionally a substrate for the enzyme as described herein; the test substance; a substituted nucleotide triphosphate in which the beta-oxygen atom is replaced by a sulfur atom (e.g., ATPβS or GTPβS) as described herein; optionally a divalent cation that binds to the substituted nucleotide triphosphate; and a reagent having at least one functional group that reacts with a thiol group of a substituted nucleotide diphosphate in which the beta-oxygen atom is replaced by a sulfur atom (e.g., ADPβS or GDPβS) (as described herein) and forms at least one reaction product (as described herein). The method typically includes reacting the reaction mixture and detecting the at least one reaction product.

Suitable test substances may include any substance suspected of having enzyme inhibitory activity. For example, a test substance may include a kinase inhibitor selected from the group consisting of bis-indoles, indolocarbazoles, phenylaminopyrimidines, balanoids, bis(indolyl)maleimides, pyridinylimidazoles, and mixtures thereof.

Also disclosed is a kit for performing the methods described herein. For example, the kit may be used for preparing a reaction mixture that is suitable for detecting enzyme activity (e.g., kinase activity, ATPase activity, and GTPase activity). The kit typically includes a substituted nucleotide triphosphate in which the beta-oxygen atom is replaced by a sulfur atom (e.g., ATPβS or GTPβS) as described herein; a reagent for detecting a substituted nucleotide diphosphate in which the beta-oxygen atom is replaced by a sulfur atom (e.g., ADPβS or GDPβS) as described herein; and optionally, a divalent cation that binds the substituted nucleotide triphosphate (e.g., ATPβS or GTPβS) and/or instructions for preparing the reaction mixture and/or detecting the substituted nucleotide triphosphate (e.g., ADPβS or GDPβS). In some embodiments, the kit may be useful for preparing a reaction mixture that is suitable for detecting enzyme activity continuously or in "real-time" (e.g., detecting ADPβS or GDPβS contemporaneously as ADPβS or GDPβS is formed in the reaction mixture). The kit may optionally include a substrate for the enzyme as described herein.

Related methods and thiol-reactive reagents for detecting enzyme activity are described in U.S. provisional application No. 60/715,114, filed on Sep. 8, 2005; Pullela et al., "Fluorescence-based detection of thiols in vitro and in vivo using dithiol probes," ANAL. BIOCHEM. (2006) 352(2):265-73; and in Chiku et al., "A Dithio Coupled Assay and ATPase assay," JOURNAL OF BIOMOLECULAR SCREENING 11(X); (2006) (accepted for publication Jun. 21, 2006); which are incorporated by reference herein in their entireties.

BRIEF DESCRIPTION OF THE DRAWINGS

FIG. 1 is a schematic representation of a DTNB-coupled kinase assay and a PK/LDH-coupled kinase assay.

FIG. 2 is a schematic representation of a DTNB-coupled reaction.

FIG. 3 represents the bathochromic shift in UV-visible absorption spectra for DTNB and NAD(P) after having been reduced.

FIG. 4 is a schematic representation of kinase reaction utilizing FRET-based reagents for detection of ADPβS.

FIG. 5 represents the elution profile for the purification of ATPβS with absorbance monitored at 260 nm for the ATPβS (βR) diastereomer collecting 13 ml fractions.

FIG. 6 is a $^{31}$P NMR spectrum of ATPβS (βR) diastereomer and ATPβS (βS) diastereomer.

FIG. 7 represents a progress curve for a DTNB-coupled assay.

FIG. 8 represents a validation curve for hydrolysis of the βS diastereomer of ATPβS by myosin after calcium activation using a DTNB-coupled assay.

FIG. 9 represents the variation of initial reaction rate for myosin hydrolysis of the βS diastereomer of ATPβS as compared to the βR diastereomer of ATPβS using a DTNB-coupled assay.

FIG. 10 represents the variation of initial reaction rate for myosin hydrolysis of ATP using a PK/LDH-coupled assay.

FIG. 11 represents a validation curve for hydrolysis of the βR diastereomer of ATPβS by hexokinase in a DTNB-coupled assay.

FIG. 12 represents the variation of initial reaction rate for hexokinase hydrolysis of the (βR) diastereomer of ATPβS as compared to the (βS) ATPβS diastereomer. FIG. 13 provides $K_M^*$ and $V_{max}^*$ for assays using ATPβS as a phosphate source as compared to ATP as a phosphate source.

FIG. 14 is a schematic representation of a BODIPY® FL L-cystine dithio reagent and a didansyl L-cystine dithio reagent.

FIG. 15 represents hydrolysis of ATPβS by calcium-activated myosin as monitored by relief of fluorescence self-quenching of didansyl L-cystine.

FIG. 16 represents hydrolysis of ATPβS by hexokinase as monitored by relief of fluorescence self-quenching of BODIPY® FL L-cystine.

FIG. 17 represents validation curves for calcium-activated myosin and hexokinase corrected for background of 0.081 and 0.506 respectively.

FIG. 18 is a schematic representation of the synthesis of a dithio reagent for detecting ADPβS.

FIG. 19 represents the fluorescence emission spectra (excitation at 489 nm) of a fluorescent dithio reagent (Rh-DAPS-FITC) at acidic (a) and basic (b) pH.

FIG. 20 displays the selected detection of ATPβS versus ATPβS by reaction with a fluorescent dithio reagent (F-DAPS-R).

FIG. 21 displays a common coupled kinase assay versus thiol-based F-DAPS-R coupled assay.

FIG. 22 displays a model of a GPCR interacting with GTPβS.

FIG. 23 displays a dithio-coupled assay of the GTPase activity of Gα using DTNB.

FIG. 24 displays exemplary "DSSA" reagents for use in dithio assay of the GTPase activity of Gα.

DETAILED DESCRIPTION

The methods disclosed herein may be used to detect enzyme activity in a reaction mixture, in particular kinase activity, ATP-hydrolase (ATPase) activity, and GTP-hydrolase (GTPase) activity. In methods used to detect enzyme activity in a sample, typically the reaction mixture will include the sample, optionally a substrate for the enzyme, a substituted nucleotide triphosphate in which the beta-oxygen atom is replaced with a sulfur atom (e.g., ATPβS or GTPβS), and a reagent for detecting a substituted diphosphate in which the beta-oxygen atom is replaced with a sulfur atom (e.g., ADPβS or GDPβS). For example, the reagent may have at least one functional group that reacts with a thiol group of ADPβS or GDPβSf to form at least one reaction product. Optionally, the reaction mixture may include divalent cations, components that form natural or artificial membranes (e.g., amphiphilic fatty acids), or detergents (e.g., non-ionic detergents like Triton® X-100 detergent or ionic detergents like SDS). The method may be performed by reacting the reaction mixture. Enzyme activity may be monitored by detecting the at least one reaction product. Detecting the at least one reaction product may include observing a change in the spectrum of the reagent. Detecting the at least one reaction product may include observing emission of light from the reagent and/or emission of light from the at least one reaction product. Detecting the at least one reaction product may include observing absorption of light by the reagent and/or absorption of light by the at least one reaction product. Detecting the at least one reaction product may include observing a change in color, a change in fluorescence, a change in phosphorescence, and/or a bathochromic shift of the reagent. Related methods and reagents for detecting enzyme activity are described in U.S. provisional application No. 60/715,114, filed on Sep. 8, 2005; Pullela et al., "Fluorescence-based detection of thiols in vitro and in vivo using dithiol probes," ANAL. BIOCHEM. (2006) 352(2):265-73; and in Chiku et al., "A Dithio Coupled Assay and ATPase assay," JOURNAL OF BIOMOLECULAR SCREENING 11(X); (2006) (accepted for publication Jun. 21, 2006); which are incorporated by reference herein in their entireties.

In other embodiments, the method may be performed by reacting a reaction mixture that includes a sample to be tested for enzyme activity, optionally a substrate for the enzyme, a substituted nucleotide triphosphate in which the beta-oxygen atom is replaced with a sulfur atom (e.g., ATPβS or GTPβS), and optionally a divalent cation that binds to the substituted nucleotide triphosphate. Optionally, the reaction mixture includes a reagent for detecting a substituted diphosphate in which the beta-oxygen atom is replaced with a sulfur atom (e.g., ADPβS or GDPβS). Alternatively, the reagent for detecting a substituted diphosphate in which the beta-oxygen atom is replaced with a sulfur atom (e.g., ADPβS or GDPβS) subsequently may be added to the reaction mixture. In some embodiments, the reagent may include at least one functional group that reacts with a thiol group of ADPβS to form at least one reaction product. Enzyme activity may be detected by detecting the at least one reaction product. Detecting the at least one reaction product may include observing emission of light from the reagent and/or emission of light from the at least one reaction product. Detecting the at least one reaction product may include observing absorption of light by the reagent and/or absorption of light by the at least one reaction product. Detecting the at least one reaction product may include observing a change in color, a change in fluorescence, a change in phosphorescence, and/or a bathochromic shift of the reagent.

As used herein, "kinase" includes any enzyme that hydrolyzes ATP to ADP (or GTP to GDP) and subsequently transferring the phosphate group of ATP (or GTP) to a suitable substrate. Suitable kinases for the methods disclosed herein typically use ATPβS or GTPβS as a phosphate source in a kinase reaction wherein ADPβS or GDPβS is thereby produced. Kinases suitable for the assay may include but are not limited to protein kinases (e.g., serine, threonine, tyrosine kinases, and/or histidine kinases), carbohydrate kinases, nucleoside/nucleotide kinases, and lipid kinases. Suitable kinases may include autokinases (i.e., kinases that exhibit autophosphorylation).

Suitable enzymes for the methods may include enzymes that convert ATP (or an analog thereof such as ATPβS or GTPβS) to ADP (or a respective analog thereof such as ADPβS or GDPβS). Suitable enzymes include ATPases and GTPases (e.g., the GTPase associated with a GPCR-complex or the Gα subunit of a GPCR-complex).

The methods disclosed herein may be useful for identifying modulators (e.g., agonist and antagonists) or G-protein coupled receptors (GPCRs). Suitable GPCRs for the methods disclose herein may include GPCRs receptors for sensory signal mediators (e.g., light and olfactory stimulatory molecules); adenosine, γ-aminobutyric acid (GABA), hepatocyte growth factor, melanocortins, neuropeptide Y, opioid peptides, opsins, somatostatin, trachykinins, vasoactive intestinal polypeptide family, and vasopressin; biogenic amines (e.g., dopamine, epinephrine and norepinephrine, histamine, glutamate (metabotropic effect), acetylcholine (muscarinic effect), and serotonin); chemokines; lipid mediators of inflammation (e.g., prostaglandins and prostanoids, platelet activating factor, and leukotrienes); and peptide hormones (e.g., bombesin, bradykinin, calcitonin, C5a anaphylatoxin, endothelin, follicle-stimulating hormone (FSH), gonadotropic-releasing hormone (GnRH), neurokinin, and thyrotropin-releasing hormone (TRH), and oxytocin). GPCRs which act as receptors for stimuli that have yet to be identified are known as orphan receptors. The methods disclosed herein may be utilized to identify activating stimuli (e.g., ligands) or modulators (e.g., agonist or antagonists) for orphan GPCR receptors.

A GPCR-complex may include a GPCR and a G-protein. A G-protein typically includes a Gα subunit and optionally may include a Gβ subunit and a Gγ subunit. The GPCR-complex may be associated with a membrane system that may include components that form natural or artificial membranes (e.g., amphiphilic fatty acids) and optionally may be solubilized in a detergent (e.g., a non-ionic detergent like Triton® X-100 detergent or an ionic detergent like SDS). A G-protein exhibits GTPase activity under suitable conditions.

The methods disclosed herein may include reacting a reaction mixture. The reaction mixture may include a reducing agent, for example, a reducing agent that reduces dithio groups (i.e., a dithio-reducing agent). Dithio-reducing agents may include phosphine-containing agents, dithiothreitol ("DTT"), beta-mercaptoethanol and mixtures thereof. In some embodiments, the selected dithio-reducing agent reduces dithio groups commonly present in proteins (e.g., oxidized di-cysteine residues) but is less efficient at reducing dithio groups present in reagents that may be useful for detecting ADPβS or GDPβS. For example, where diaryl disulfide reagents are used for detecting ADPβS or GDPβS in the reaction mixture, the selected dithio-reducing agent may include a phosphine-containing agent that has been shown to reduce diaryl disulfides relatively slowly as compared to dithio groups commonly present in proteins. Desirably, the dithio-reducing agent includes a phosphine-containing agent. In one embodiment, the dithio-reducing agent includes a phosphine having the formula:

in which X, Y, and Z, independently are selected from the group consisting of hydrogen, alkyl, alkenyl, alkynyl, aryl, and carboxyalkyl. The dithio-reducing agent may include a phosphine such as Tris(2-carboxyethyl)phosphine ("TCEP").

The reaction mixture may include components commonly present in reaction mixtures that are suitable for performing enzyme assays. For example, die reaction mixture may include at least one of salt (e.g., NaCl, KCl), buffer (e.g., Tris, Tris-HCl), thickening agent (e.g., glycerol) and/or a carrier (e.g., a non-enzymatic protein or carbohydrate carrier).

The method may be useful for performing continuous assays (i.e., real-time assays). As used herein, "continuous assays" and "real-time assays" include assays in which at least one reaction product is detected in a reaction mixture contemporaneously as the product is formed in the reaction mixture. As such, the at least one reaction product may include a label useful for performing continuous assays (i.e., real-time assays).

As used herein, a "label" may include any suitable agent for detecting at least one reaction product in a reaction mixture. For example, a label may include but is not limited to a fluorophore, a chromophore, a radiolabel (which may include a radioisotope), and a scintillant.

As used herein, a "fluorophore" is a chemical group that can be excited by light to emit fluorescence. Some fluorophores may be excited by light to emit phosphorescence. As used herein, a "dye" may include a fluorophore. Suitable fluorophores may include but are not limited to: 1,5 IAEDANS; 1,8-ANS; 4-Methylumbelliferone; 5-carboxy-2, 7-dichlorofluorescein; 5-Carboxyfluorescein (5-FAM); 5-Carboxytetramethylrhodamine (5-TAMRA); 5-HAT (Hydroxy Tryptamine); 5-Hydroxy Tryptamine (HAT); 5-ROX (carboxy-X-rhodamine); 6-Carboxyrhodamine 6G; 6-CR 6G; 6-JOE; 7-Amino-4-methylcoumarin; 7-Aminoactinomycin D (7-AAD); 7-Hydroxy-4-methylcoumarin; 9-Amino-6-chloro-2-methoxyacridine; ABQ; Acid Fuchsin; ACMA (9-Amino-6-chloro-2-methoxyacridine); Acridine Orange; Acridine Red; Acridine Yellow; Acriflavin; Acriflavin Feulgen SITSA; Alexa Fluor 350™; Alexa Fluor 430™; Alexa Fluor 488™; Alexa Fluor 532™; Alexa Fluor 546™; Alexa Fluor 568™; Alexa Fluor 594™; Alexa Fluor 633™; Alexa Fluor 647™; Alexa Fluor 660™; Alexa Fluor 680™; Alizarin Complexon; Alizarin Red; Allophycocyanin (APC); AMC; AMCA-S; AMCA (Aminomethylcoumarin); AMCA-X; Aminoactinomycin D; Aminocoumarin; Aminomethylcoumarin (AMCA); Anilin Blue; Anthrocyl stearate; APC (Allophycocyanin); APC-Cy7; APTS; Astrazon Brilliant Red 4G; Astrazon Orange R; Astrazon Red 6B; Astrazon Yellow 7 GLL; Atabrine; ATTO-TAG™ CBQCA; ATTO-TAG™ FQ; Auramine; Aurophosphine G; Aurophosphine; BAO 9 (Bisaminophenyloxadiazole); Berberine Sulphate; Beta Lactamase; BFP blue shifted GFP (Y66H); Blue Fluorescent Protein; BFP/GFP FRET; Bimane; Bisbenzamide; Bisbenizimiide (Hoechst); Blancopihor FFG; Blancoplior SV; BOBO™-1; BOBO™-3; Bodipy 492/515; Bodipy 493/503; Bodipy 500/510; Bodipy 505/515; Bodipy 530/550; Bodipy 542/563; Bodipy 558/568; Bodipy 564/570; Bodipy 576/589; Bodipy 581/591; Bodipy 630/650-X; Bodipy 650/665-X; Bodipy 665/676; Bodipy FL; Bodipy FL ATP; Bodipy Fl-Ceramide; Bodipy R6G SE; Bodipy TMR; Bodipy TMR-X conjugate; Bodipy TMR-X, SE; Bodipy TR; Bodipy TR ATP; Bodipy TR-X SE; BO-PRO™-1; BO-PRO™-3; Brilliant Sulphoflavin FF; Calcein; Calcein Blue; Calcium Crimson™; Calcium Green; Calcium Orange; Calcofluor White; Cascade Blue™; Cascade Yellow; Catecholamine; CCF2 (GeneBlazer); CFDA; CFP—Cyan Fluorescent Protein; CFP/YFP FRET; Chlorophyll; Chromomycin A; CL-NERF (Ratio Dye, pH); CMFDA; Coelenterazine f; Coelenterazine fcp; Coelenterazine h; Coelenterazine hcp; Coelenterazine ip; Coelenterazine n; Coelenterazine O; Coumarin Phalloidin; C-phycocyanine; CPM Methylcoumarin; CTC; CTC Formazan; Cy2™; Cy3.18; Cy3.5™; Cy3™; Cy5.18; Cy5.5™; Cy5™; Cy7™; Cyan GFP; cyclic AMP Fluorosensor (FiCRhR); Dabcyl; Dansyl; Dansyl Amine; Dansyl Cadaverine; Dansyl Chloride; Dansyl DHPE; Dansyl fluoride; DAPI; Dapoxyl; Dapoxyl 2; Dapoxyl 3; DCFDA; DCFH (Dichlorodihydrofluorescein Diacetate); DDAO; DHR (Dihydrorhodamine 123); Di-4-ANEPPS; Di-8-ANEPPS (non-ratio); DiA (4-Di-16-ASP); DiD-Lipophilic Tracer-DiD (DiIC18 (5)); DIDS; DiI (DiIC18(3)); Dinitrophenol; DiO (DiOC18 (3)); DiR; DiR (DiIC18(7)); DNP; Dopamine; DsRed; DTAF; DY-630-NHS; DY-635—NHS; EBFP; ECFP; EGFP; ELF 97; Eosin; Erythrosin; Erythrosin ITC; Ethidium Bromide; Ethidium homodimer-1 (EthD-1); Euchrysin; EukoLight; Europium (III) chloride; EYFP; Fast Blue; FDA; Feulgen (Pararosaniline); FITC; Flazo Orange; Fluo-3; Fluo-4; Fluorescein (FITC); Fluorescein Diacetate; Fluoro-Emerald; Fluoro-Gold (Hydroxystilbamidine); Fluor-Ruby; Fluor X; FM 1-43™; FM 4-46; Fura Red™; Fura Red™/Fluo-3; Fura-2; Fura-2/BCECF; Genacryl Brilliant Red B; Genacryl Brilliant Yellow 10GF; Genacryl Pink 3G; Genacryl Yellow 5GF; GeneBlazer (CCF2); GFP(S65T); GFP red shifted (rsGFP); GFP wild type, non-UV excitation (wtGFP); GFP wild type, UV excitation (wtGFP); GFPuv; Gloxalic Acid; Granular Blue; Haematoporphyrin; Hoechst 33258; Hoechst 33342; Hoechst 34580; HPTS; Hydroxycoumarin; Hydroxystilbamidine (FluoroGold); Hydroxytryptamine; Indo-1; Indodicarbocyanine (DiD); Indotricarbocyanine (DiR); Intrawhite Cf; JC-1; JO-JO-1; JO-PRO-1; Laurodan; LDS 751 (DNA); LDS 751 (RNA); Leucophor PAF; Leucophor SF; Leucophor WS; Lissamine Rhodamine; Lissamine Rhodamine B; Calcein/Ethidium homodimer; LOLO-1; LO-PRO-1; Lucifer Yellow; Lyso Tracker Blue; Lyso Tracker Blue-White; Lyso Tracker Green; Lyso Tracker Red; Lyso Tracker Yellow; LysoSensor Blue; LysoSensor Green; LysoSensor Yellow/Blue; Mag Green; Magdala Red (Phloxin B); Mag-Fura Red; Mag-Fura-2; Mag-Fura-5; Mag-Indo-1; Magnesium Green; Magnesium Orange; Malachite Green; Marina Blue; Maxilon Brilliant Flavin 10 GFF; Maxilon Brilliant Flavin 8 GFF; Merocyanin; Methoxycoumarin; Mitotracker Green FM; Mitotracker Orange; Mitotracker Red; Mitramycin; Monobromobimane; Monobromobimane (mBBr-GSH); Monochlorobimane; MPS (Methyl Green Pyronine Stilbene); NBD; NBD Amine; Nile Red; Nitrobenzoxadidole; Noradrenaline; Nuclear Fast Red; Nuclear Yellow; Nylosan Brilliant lavin E8G; Oregon Green; Oregon Green 488-X; Oregon Green™; Oregon Green™ 488; Oregon Green™ 500; Oregon Green™ 514; Pacific Blue; Pararosaniline (Feulgen); PBFI; PE-Cy5; PE-Cy7; PerCP; PerCP-Cy5.5; PE-TexasRed [Red 613]; Phloxin B (Magdala Red); Phorwite AR; Phorwite BKL; Phorwite Rev; Phorvite RPA; Phosphine 3R; Phycoerythrin B [PE]; Phycoerythrin R [PE]; PKH26 (Sigma); PKH67; PMIA; Pontochrome Blue Black; POPO-1; POPO-3; PO-PRO-1; PO-PRO-3; Primuline; Procion Yellow; Propidium Iodid (PI); PyMPO; Pyrene; Pyronine; Pyronine B; Pyrozal Brilliant Flavin 7GF; QSY 7; Quinacrine Mustard; Red 613 [PE-TexasRed]; Resorufin; RH 414; Rhod-2; Rhodamine; Rhodamine 110; Rhodamine 123; Rhodamine 5 GLD; Rhodamine 6G; Rhodamine B; Rhodamine B 200; Rhodamine B extra; Rhodamine BB; Rhodamine BG; Rhodamine Green; Rhodamine Phallicidine; Rhodamine Phalloidine; Rhodamine Red; Rhodamine WT; Rose Bengal; R-phycocyanine; R-phycoerythrin (PE); RsGFP; S65A; S65C; S65L; S65T; Sapphire GFP; SBFI; Serotonin; Sevron Brilliant Red 2B; Sevron Brilliant Red 4G; Sevron Brilliant Red B; Sevron Orange; Sevron Yellow L; sgBFP™; sgBFP™ (super glow BFP); sgGFP™; sgGFP™ (super glow GFP); SITS; SITS (Primuline); SITS (Stilbelle Isothiosulphonic Acid); SNAFL calcein; SNAFL-1; SNAFL-2; SNARF calcein; SNARFl; Sodium Green; SpectrumAqua; SpectrumGreen; SpectrumOrange; Spectrum Red; SPQ (6-methoxy-N-(3-sulfopropyl)quinolinium); Stilbene; Sulphorhodamine B can C; Sulphorhodamine G Extra; SYTO 11; SYTO 12; SYTO 13; SYTO 14; SYTO 15; SYTO 16; SYTO 17; SYTO 18; SYTO 20; SYTO 21; SYTO 22;

SYTO 23; SYTO 24; SYTO 25; SYTO 40; SYTO 41; SYTO 42; SYTO 43; SYTO 44; SYTO 45; SYTO 59; SYTO 60; SYTO 61; SYTO 62; SYTO 63; SYTO 64; SYTO 80; SYTO 81; SYTO 82; SYTO 83; SYTO 84; SYTO 85; SYTOX Blue; SYTOX Green; SYTOX Orange; Tetracycline; Tetramethylrhodamine (TRITC); Texas Red™; Texas Red-X™ conjugate; Thiadicarbocyanine (DiSC3); Thiazine Red R; Thiazole Orange; Thioflavin 5; Thioflavin S; Thioflavin TCN; Thiolyte; Thiozole Orange; Tinopol CBS (Calcofluor White); TMR; TO-PRO-1; TO-PRO-3; TO-PRO-5; TOTO-1; TOTO-3; TriColor (PE-Cy5); TRITC TetramethylRodaminelsoThioCyanate; True Blue; TruRed; Ultralite; Uranine B; Uvitex SFC; wt GFP; WW 781; X-Rhodamine; XRITC; Xylene Orange; Y66F; Y66H; Y66W; Yellow GFP; YFP; YO-PRO-1; YO-PRO-3; YOYO-1; and YOYO-3. As used herein, a "fluorophore" may include a salt of the fluorophore. Fluorophores may include isothiocyanate derivatives and/or succinimidyl ester derivatives of the fluorophore.

As used herein, a "chromophore" is a chemical group that absorbs light which results in the display of visible color. As used herein, a "dye" include a chromophore. Suitable chromophores may include any useful chromophore as known in the art. The chromophore may include but is not limited to 5-mercapto-2-nitrobenzoic acid. Chromophores may include fluorophores. As used herein, a "chromophore" may include a salt of the chromophore. Chromophores may include isothiocyanate derivatives and/or succinimidyl ester derivatives of the chromophore.

Suitable radioisotopes may include any radioisotope that is suitable for labeling and detecting a reaction product. For example, suitable radioisotopes may include but are not limited to $^3$H, $^{14}$C, $^{35}$S, $^{32}$P, $^{33}$P, $^{125}$I, and $^{131}$I. Suitable radioisotopes may include salts of the radioisotope.

The reagent used for detecting ADPβS may include a dithio reagent. As used herein, "dithio" means the chemical group —S—S—. A "dithio reagent" is a reagent that includes the chemical group —S—S—. As used herein, "dithio" may be used interchangeably with "disulfide" or "disulphide."

The reagent may have a formula $R^1$—S—S—$R^2$. In some embodiments, $R^1$ and $R^2$ are the same or different, and at least one of $R^1$ and $R^2$ includes a label. The at least one reaction product of the reagent and ADPβS may have a formula selected from the group consisting of ADPβS-S—R', ADPβS-S—$R^2$, GDPβS-S—R', GDPβS-S—$R^2$, $R^1$—S—H, $R^2$—S—H, and salts thereof. As used herein, "salts thereof" may include ionized forms of the at least one reaction product such as $R^1$—S$^-$ and $R^2$—S$^-$.

The reagent may include groups that exhibit fluorescence resonance energy transfer ("FRET"). For example, the reagent may have a formula $R^1$—S—S—$R^2$, in which $R^1$ may include a first fluorophore and $R^2$ may include a second fluorophore. The first fluorophore may have an emission spectrum and the second fluorophore may have an absorption spectrum, such that the emission spectrum and the absorption spectrum overlap. The emission spectrum and the absorption spectrum may overlap by at least about 10%, and desirably the emission spectrum and the absorption spectrum may overlap by at least about 20%, 30%, 40%, or 50%. In some embodiments, the first fluorophore and the second fluorophore are present in the reagent at a distance of about 10-100 angstroms, and preferably 25-75 angstroms or more preferably about 30-70 angstroms. Desirably, the first fluorophore emits fluorescence that is quenched by the second fluorophore and/or that stimulates emission by the second fluorophore. In further embodiments, the first fluorophore and the second fluorophore are present in the reagent at a distance of about 3-100 angstroms, and preferably 3-75 angstroms or more preferably about 3-50 angstroms. Desirably, the first fluorophore emits fluorescence that is quenched by the second fluorophore and/or that stimulates emission by the second fluorophore.

The reagent may also exhibit self-quenching in a fluorescence assay. For example, the reagent may have a formula $R^1$—S—S—$R^2$, in which $R^1$ and $R^2$ comprise identical fluorophores that exhibit self-quenching. In some embodiments, detecting the at least one reaction product may include observing a decrease in self-quenching. In some embodiments, detecting the at least one reaction product may include observing fluorescence polarization or depolarization.

The reagent may also exhibit self-quenching and/or fluorescence polarization. For example, the reagent may have a formula $R^1$—S—S—$R^2$, in which $R^1$ and $R^2$ comprise identical fluorophores that exhibit self-quenching and/or fluorescence polarization. In some embodiments, detecting the at least one reaction product may include observing a decrease in self-quenching and/or observing a decrease in fluorescence polarization or depolarization.

In another example, the reagent may have a formula $R^1$—S—S—$R^2$, in which $R^1$ may include a first fluorophore and $R^2$ may include a second fluorophore. The second fluorophore may have a molecular weight that is significantly larger than the molecular weight of the first fluorophore. For example, the second fluorophore may have a molecular weight that is at least about 2× the molecular weight of the first fluorophore, (preferably at least about 4× the molecular weight of the first fluorophore or at least about 6× the molecular weight of the first fluorophore), and detecting the at least one reaction product may include observing a decrease or increase in fluorescence polarization or depolarization (e.g., detecting a decrease in fluorescence polarization of the first fluorophore).

In another example, the reagent may have a formula $R^1$—S—S—$R^2$, in which $R^1$ may include a fluorophore and $R^2$ may include a non-fluorophore. The non-fluorophore may have a molecular weight that is significantly larger than the molecular weight of the fluorophore. For example, the non-fluorophore may have a molecular weight that is at least about 2× the molecular weight of the fluorophore, (preferably at least about 4× the molecular weight or the fluorophore or al least about 6× the molecular weight of the fluorophore), and detecting the at least one reaction product may include observing an increase or decrease in fluorescence polarization or depolarization (e.g., detecting a decrease in fluorescence polarization of the fluorophore). The non-fluorophore may include a protein (e.g., a protein with one surface-exposed thiol present on a cysteine amino acid).

The reagent may also include a fluorophore and a non-fluorophore. For example, the reagent may have a formula $R^1$—S—S—$R^2$, in which $R^1$ may include a fluorophore and $R^2$ may include a non-fluorophore. In some embodiments, the fluorophore has an emission spectrum and the non-fluorophore has an absorption spectrum such that the emission spectrum and absorption spectrum overlap. In some embodiments, the fluorophore and the non-fluorophore are present in the reagent at a distance of about 10-100 angstroms, and preferably 25-75 angstroms or more preferably about 30-70 angstroms. In further embodiments, the fluorophore and the non-fluorophore are present in the reagent at a distance of about 3-100 angstroms, and preferably 3-75 angstroms or more preferably about 3-50 angstroms. In some embodiments, detecting the at least one reaction product may include observing dequenching of the fluorophore. The non-fluorophore may include a chromophore. The non-fluorophore may include a black hole quencher ("BHQ"), as commonly known in the art.

The reagent may include a radioisotope as described herein and a scintillant. For example, the reagent may be useful for performing a scintillation proximity assay ("SPA"). In some embodiments, the reagent may have a formula $R^1$—S—S—$R^2$, in which one of $R^1$ and $R^2$ includes a radiolabel and the other of $R^1$ and $R^2$ includes a scintillant. As used herein, a "scintillant" is any agent that produces a photon when exposed to an energetic particle (e.g., an energetic particle emitted by a radioisotope). Suitable scintillants may include but are not limited to organic scintillants.

The reagent typically is a dithio reagent. In some embodiments, the reagent may have the formula $R^1$—S—S—$R^2$, wherein $R^1$—S—S—$R^2$ are linked by a dithio linker group. In some embodiments, $R^1$ and $R^2$ may be linked by a dithio linker group that includes one or more aryl groups. For example, the reagent may have the formula $R^1$-$A^1$-S—S-$A^2$-$R^2$ in which $R^1$ and $R^2$ are the same or different; at least one of $R^1$ and $R^2$ includes a label; and at least one of $A^1$ and $A^2$ includes an aryl group. In some embodiments, the aryl group may be selected from a phenyl group and a pyridinyl group. The reagent may have the formula:

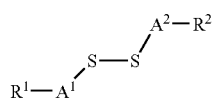

$A^1$ and $A^2$ may be the same or different and at least one of $A^1$ and $A^2$ may include an aryl group. In some embodiments at least one of $A^1$ and $A^2$ includes any aryl group selected from a phenyl group and a pyridinyl group, which may be substituted. For example, at least one of $A^1$ and $A^2$ may include an aryl substituted with an amide group. In some embodiments at least one of $A^1$ and $A^2$ includes a group having a formula selected from:

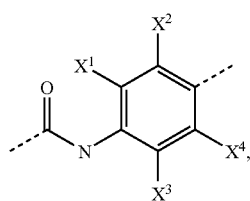

and

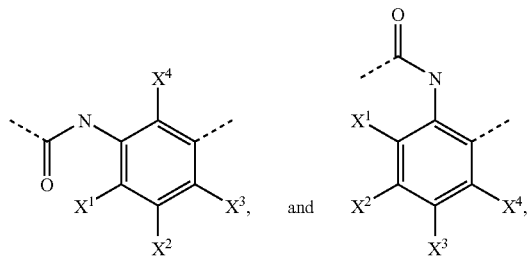

wherein $X^1$, $X^2$, $X^3$, and $X^4$ may be the same or different and are hydrogen or halide (i.e., F, Cl, Br, or I).

In one suitable embodiment, at least one of $A^1$ and $A^2$ includes a group having a formula:

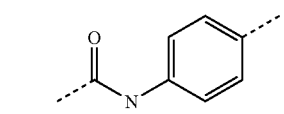

The reagent may have a formula:

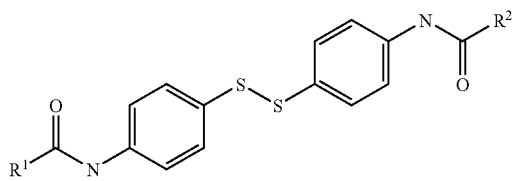

In the formula, $R^1$ and $R^2$ may be the same or different and at least one of $R^1$ and $R^2$ includes a label. In one embodiment, at least one of $R^1$ and $R^2$ includes a fluorophore. The other of $R^1$ and $R^2$ may include a group independently selected from a second fluorophore, a non-fluorophore that quenches the fluorophore, a second fluorophore or non-fluorophore that is significantly larger than the fluorophore. $R^1$ may include a first fluorophore and $R^2$ may include a second fluorophore or non-fluorophore such that the first fluorophore and second fluorophore or non-fluorophore exhibit FRET and/or fluorescence quenching and/or fluorescence depolarization. For example $R^1$ may include a fluorescein group (such as a fluorescein group present in fluorescein isothiocyanate or a salt thereof) and $R^2$ may include a rhodamine group (such as a rhodamine group present in rhodamine B or as salt thereof). $R^1$ and $R^2$ may include an identical fluorophore that exhibits self-quenching or fluorescence polarization. In the formula, at least one of $R^1$ and $R^2$ may include a radiolabel, and the other of $R^1$ and $R^2$ may include a scintillant. For example, at least one of $R^1$ and $R^2$ may include a radioisotope and the other of $R^1$ and $R^2$ may include a scintillant such that the scintillant emits light in the intact reagent but does not emit light when the disulfide bond of the reagent is hydrolyzed.

The reagent may include dithionitrobenzoic acid ("DTNB" or "Ellmans's reagent"). The methods described herein may include methods suitable for performing DTNB-coupled assays. (See FIG. 1 and FIG. 2). DTNB-coupled assays may be performed where the reaction mixture includes DTNB. The reagent may be used to detect enzyme activity wherein the reagent (or a chromophore present in the reagent) undergoes a bathochromic shift in maximum absorbance wavelength when the reagent is reduced upon reacting with ADPβS. (See FIG. 3).

The reagent may include a FRET dithio reagent having a formula $R^1$—S—S—$R^2$, wherein $R^1$ includes a fluorescein-type fluorophore and $R^2$ includes a rhodamine-type fluorophore. Fluorescein-type fluorophores may include fluorescein, FITC, Oregon green 488 and Oregon green 514. Rhodamine-type fluorophores may include non-fluorescent quenchers such as QSY dyes. In one embodiment, the reagent may have a formula:

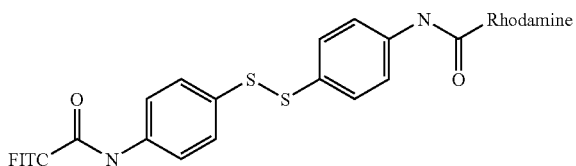

A FRET-based dithio assay may be performed under similar conditions as described for DTNB-coupled assays. However, FRET-based dithio assays typically will utilize dithio linked donor-acceptor pairs that are reduced by ADPβS produced as a reaction product in an enzyme reaction such as a kinase reaction. (See FIG. 4). The reaction may be monitored using a fluorescent plate reader (BMG Polarstar) or imaging device (Typhoon) that detects fluorescence in FRET assays. By reducing the disulfide that links a donor-acceptor pair, the FRET effect is eliminated. Typically, the donor and acceptor will be within 10-100 Å in the intact FRET dithio reagent; the absorption spectrum of acceptor and emission spectrum of donor will overlap; and the donor-acceptor transition dipole orientations will be parallel for a significant fraction of time during the assay. One parameter in a FRET reagent is the Forster radius, which may be defined as the distance at which energy transfer is 50% efficient, and is given by the equation:

$$R_o = [8.8 \times 10^{23} * \kappa^2 * n^4 QY_D * J(\lambda)]^{1/6} \text{ Å}$$

where n is the refractive index, $J(\lambda)$ is the spectral overlap integral, $\kappa^2$ is the dipole orientation factor (2/3 if randomly oriented), and $QY_D$ is the quantum yield for the donor in the absence of the acceptor.

For DTNB-coupled assays, UV/V is absorbance may be monitored at the maximum absorbance wavelength for DTNB (approximately $\lambda$=412 nm). For fluorescence quenching assays, fluorescence may be monitored at the emission maximum for the excited fluorescent group. For fluorescence polarization assays, changes in fluorescence polarization may be measured for the fluorescent group that is excited, as known in the art. For FRET-based assays, fluorescence may be monitored at an appropriate maximum emission wavelength for an acceptor fluorophore present in the reagent, after excitation of the donor fluorophore that is also present in the reagent, as known in the art.

Dithio-linked BODIPY (molecular probes, B-20340), which shows intramolecular quenching until reduced by free thiols, may be utilized in fluorescence-quenching assays. Alternatively, and in a preferred embodiment, FRET reagents that include disulfide linked donor-acceptor pairs may be synthesized by methods known in the art. For example, amine-reactive dyes containing groups such as isothiocyanates (yielding thioureas) or succinimidyl esters (yielding carboxamides) may be reacted with linkers that contain both amine and thiol groups, whereby the amine reacts to form the thiourea or carboxamide, and the thiol remains unreacted. Reactions may be performed with reagents that contain both the amine and thiol functionality, taking advantage of the preferential reactivity of the amine with these functional groups. The individual D-S and A-S groups may be coupled by subjecting them to oxidizing conditions in order to form the D-S-S-D, D-S-S-A and A-S-S-A pairs. In another embodiment, the amine reactive dyes may be reacted with an oxidized dithio form of the amine and thio containing linker. To separate reaction products (e.g., D-S-S-D, D-S-S-A and A-S-S-A, where D—donor and A=acceptor), HPLC, silica gel chromatography, or other purification strategies may be used. Useful reagents for synthesizing FRET reagents may include: (a) cysteine (as used by Molecular Probes to make a dithio reagent with BODIPY) and (b) β-mercaptoethanieamine (Sigma-Aldrich) or 4-mercaptoaniline. Possible FRET donor-acceptor pairs to be created as dithio reagents are shown in TABLE 1.

TABLE 1

| Donor | Acceptor | $R_0$ |
| --- | --- | --- |
| Alexa 488 | Alexa 555 | 70 |
| Alexa 488 | Alexa 647 | 56 |
| Fluorescein | tetramethylrhodamine | 55 |
| Fluorescein | Fluorescein | 44 |
| BODIPY FL | BODIPY FL | 57 |

In a FRET disulfide reagent in which the donor and acceptor are different, the donor may be excited and either: (a) quenching of donor fluorescence or (b) fluorescence of acceptor, may be detected. In some embodiments, fluorescence polarization or depolarization may be detected. Non-fluorescent acceptors may be utilized in the reagent to quench fluorescence.

FRET assays may be performed in plates using any fluorescent plate reader with appropriate filters, such as the BMG Polarstar. Appropriate assay conditions may be identified by performing a FRET assay in any suitable plate (e.g., 96 well plates). Any suitable enzyme may be assayed in plates, (e.g., cAMP dependent protein kinase, any MAP kinase, PKC, caseine kinase II, small molecule kinases such as acetate kinase and pyruvate kinase, ATPases, and GTPases such as Gα subunit of a GPCR-complex). Assays in plates may be performed in the presence of a suitable phosphate source, ATPβS or GTPβS (including the (βR) and/or (βS) diastereomer) and a suitable dithio FRET reagent.

The enzyme assays described herein may be modified for use in gels (e.g., 1D or 2D gels), for applications involving functional genomics, as well as assay of crude protein samples. Any suitable enzyme may be utilized in the in gel assay. Suitable tissue samples may be utilized in the in gel assay by making tissue homogenates, and clarifying the sample by centrifugation. An enzyme or a sample that is suspected of containing an enzyme may be loaded onto an SDS PAGE gel (either 1D or 2D) and electrophoretically separated. The enzyme then may be renatured using established protocols. The gel then may be soaked in an assay solution as described herein or as known in the art. Fluorescence measurements may then be performed using a fluorescence imaging device, such as an Amersham Storm or Typhoon fluorescence reader. Conditions for renaturation and assay may be optimized for maximum sensitivity, as expected based on stereoselectivity for the (βR) or (βS) diastereomer in the assay. When the (βS) diastereomer of ATPβS or GTPβS is used in the methods described herein with a FRET dithio reagent, an observed change in FRET should be observed for any enzyme specific for the (βS) diastereomer of ATPβS or GTPβS, but not for enzymes that are specific for the (βR) diastereomer of ATPβS or GTPβS. It is known in the art that kinases are typically specific for one or the other diastereomer of ATPβS.

The in gel assay may be performed in the presence of test substrates to identify potential enzyme inhibitors. The reaction rate for all enzymes in the gel may be monitored, providing a broad and parallel specificity check for the inhibitor.

The methods described herein may be performed in cells and/or tissues. The methods described herein may be performed in sill.

The methods disclosed herein may include reacting a reaction mixture that includes a phosphate source. As defined herein, a "phosphate source" is any agent that includes a phosphate group ($PO_4^{3-}$) that is transferred by a kinase to a substrate or hydrolyzed from the phosphate source by an ATPase or GTPase. A phosphate source may include ATP or desirably, an analog of ATP such as ATPβS or GTPβS. Where the reaction mixture includes ATPβS or GTPβS, the ATPβS or GTPβS may comprise a mixture of diastereomers, and the ATPβS or GTPβS may be enriched in one or more diastereomers. For example, in some embodiments, the ATPβS or GTPβS may have a (βS) diastereomer content of at least about 80%, preferably at least about 90% or more preferably at least about 95%. In some embodiments, the ATPβS or GTPβS may have a (βR) diastereomer content of at least about 80%, preferably at least about 90% or more preferably at least about 95%. Methods for synthesizing diastereomers of ATPβS and GTPβS are known in the art and are described herein.

The reaction mixture optionally includes a suitable substrate. As described herein, a suitable substrate may include a polypeptide, a carbohydrate, a nucleotide, a fatty acid and/or water. Polypeptides may include polypeptides that include at least one of serine, threonine, tyrosine, and histidine. As defined herein, a "substrate" for a kinase includes any agent that is phosphorylated by a suitable kinase.

The methods described herein may be useful for identifying agents that modulate the activity of an enzyme, for example, as screening methods. A modulator may include an agent that inhibits enzyme activity or an agent that enhances enzyme activity. For example, the reaction mixture may include the enzyme; optionally a substrate for the enzyme as described herein; the test substance; ATPβS or GTPβS as described herein; and a reagent having at least one functional group that reacts with a thiol group of ADPβS or GDPβS (as described herein) and forms at least one reaction product (as described herein). The method typically includes reacting the reaction mixture and detecting the at least one reaction product. By comparing enzyme activity in the presence of the test substance versus in the absence of the test substance, a modulator of enzyme activity may be identified. Optionally, the reaction mixture may include components such as divalent cations, components that form natural or artificial membranes (e.g., amphiphilic fatty acids), and detergents (e.g., non-ionic detergents like Triton® X-100 detergent or ionic detergents like SDS).

Suitable test substances may include any substance suspected of having enzyme inhibitory activity. For example, kinase inhibitors are known in the art and may include SB203580, staurosporine, Gleevac, Tamoxifen, Bryostatin, VX-745, and BIRB796. These inhibitors may be derivatized by methods known in the art, (e.g., alkylated, halogenated, carboxylated, and/or acetylated) and tested in the methods described herein (e.g., in screening methods). In some embodiments, the test substance may be selected from classes of agents that are known to exhibit kinase inhibitory activity. For example, a test substance may include a kinase inhibitor selected from the group consisting of bis-indoles, indolocarbazoles, phenylaminopyrimidines, balanoids, bis(indolyl)maleimides, pyridinylimidazoles, and mixtures thereof.

Kits may be assembled that are useful for practicing the disclosed methods. For example, a kit for preparing a reaction mixture that is suitable for detecting enzyme activity may be assembled. As such, the kits may include one or more components that are utilized in the methods. The kits disclosed herein may include at least one component selected from the following components: ATPβS as described herein (e.g., comprising a mixture of diastereomers which may have an enhanced content of a diastereomer); a divalent metal cation (such as $Mg^{2+}$, $Cd^{2+}$, $Co^{2+}$, $Mn^{2+}$ and $Cr^{2+}$); a reagent comprising at least one functional group that reacts with a thiol group of ADPβS (as described herein) and forms at least one reaction product (as described herein); and optionally, instructions for preparing the reaction mixture and detecting the at least one reaction product. The kit may be useful for preparing a reaction mixture that is suitable for detecting enzyme activity continuously or in "real-time" (e.g., detecting the at least one reaction product contemporaneously as the at least one reaction product is formed in the reaction mixture). The kit may optionally include a substrate for the enzyme (as described herein). The kit may optionally include components selected from salts (which may be in solution), buffer (which may be in solution), and carriers (which may include a non-enzymatic protein and/or carbohydrate in solution).

ILLUSTRATIVE EMBODIMENTS

The following embodiments are illustrative and not intended to limit the claimed subject matter.

Embodiment 1

A method for detecting kinase activity in a reaction mixture comprising (a) reacting the reaction mixture, the reaction mixture comprising: (i) a substrate for the kinase; (ii) ATPβS or GTPβS; (iii) a divalent cation that binds to ATPβS or GTPβS; (iv) a reagent comprising at least one functional group that reacts with a thiol group of ADPβS or GDPβS and forms at least one reaction product; and (b) detecting the a least one reaction product.

Embodiment 2

The method of embodiment 1, the reaction mixture further comprising a thiol-reducing agent.

Embodiment 3

The method of embodiment 2, the thiol-reducing agent comprising a phosphine.

Embodiment 4

The method of embodiment 3, the phosphine having the formula

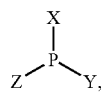

X, Y, and Z, independently are selected from the group consisting of —H, alkyl, alkenyl, alkynyl, aryl, and carboxyalkyl.

Embodiment 5

The method of embodiment 4, the phosphine comprising Tris(2-carboxyethyl)phosphine.

Embodiment 6

The method of embodiment 2, wherein the thiol-reducing agent comprised beta-mercaptoethanol.

Embodiment 7

The method of embodiment 1, wherein detecting the at least one reaction product is performed contemporaneously as the at least one reaction product is formed.

Embodiment 8

The method of embodiment 1, wherein the at least one reaction product comprises a label.

Embodiment 9

The method of embodiment 8, wherein the label comprises a fluorophore, a chromophore, or both.

Embodiment 10

The method of embodiment 8, wherein the label comprises a fluorophore and a chromophore.

Embodiment 11

The method of embodiment 8, wherein the label comprises a fluorophore.

Embodiment 12

The method of embodiment 11, wherein the fluorophore comprises fluorescein or rhodamine.

Embodiment 13

The method of embodiment 11, wherein the fluorophore comprises pyrromethene boron difluoride.

Embodiment 14

The method of embodiment 11, wherein the fluorophore comprises a dansyl group.

Embodiment 15

The method of embodiment 8, wherein the label comprises a chromophore.

Embodiment 16

The method of embodiment 15, wherein the chromophore comprises 5-mercapto-2-nitrobenzoic acid.

Embodiment 17

The method of embodiment 1, wherein the reagent has a formula $R^1$—S—S—$R^2$; $R^1$ and $R^2$ are the same or different; and at least one of $R^1$ and $R^2$ comprises a label.

Embodiment 18

The method of embodiment 17, wherein the at least one reaction product has a formula selected from the group consisting of ADPβS-S—$R^1$, ADPβS-S—$R^2$, $R^1$—S—H, $R^2$—S—H, and salts thereof.

Embodiment 19

The method of embodiment 17, wherein $R^1$ comprises a first fluorophore and $R^2$ comprises a second fluorophore.

Embodiment 20

The method of embodiment 19, the first fluorophore having an emission spectrum and the second fluorophore having an absorption spectrum, such that the emission spectrum and the absorption spectrum overlap.

Embodiment 21

The method of embodiment 20, wherein the emission spectrum and the absorption spectrum overlap by at least about 10%, 20%, 30%, 40%, or 50%.

Embodiment 22

The method of embodiment 20, wherein the first fluorophore and the second fluorophore are present in the reagent at a distance of about 10-100 angstroms, preferably 25-75 angstroms, more preferably about 30-70 angstroms.

Embodiment 23

The method of embodiment 17, wherein $R^1$ and $R^2$ comprise identical fluorophores.

Embodiment 24

The method of embodiment 23, wherein detecting the at least one reaction product comprises observing a decrease in self-quenching.

Embodiment 25

The method of embodiment 19 or 23, wherein detecting the at least one reaction product comprises observing a change in fluorescence polarization.

Embodiment 26

The method of embodiment 19, wherein detecting the at least one reaction product comprises observing dequenching of the first fluorophore.

Embodiment 27

The method of embodiment 20, wherein detecting the at least one reaction product comprises observing a decrease in sensitized fluorescence of the second fluorophore.

Embodiment 28

The method of embodiment 17, wherein $R^1$ comprises a fluorophore having an emission spectrum and $R^2$ comprises a non-fluorophore having an absorption spectrum such that the emission spectrum and absorption spectrum overlap.

Embodiment 29

The method of embodiment 28, wherein the fluorophore and the non-fluorophore are present in the reagent at a distance of about 3-100 angstroms, preferably 3-75 angstroms, more preferably about 3-50 angstroms.

Embodiment 30

The method of embodiment 28, wherein detecting the at least one reaction product comprises observing dequenching of the fluorophore.

Embodiment 31

The method of embodiment 28, wherein the non-fluorophore comprises a chromophore.

Embodiment 32

The method of embodiment 17, wherein $R^1$ comprises a first fluorophore and $R^2$ comprises a second fluorophore, the second fluorophore having a molecular weight that is at least about 2× the molecular weight of the first fluorophore.

Embodiment 33

The method of embodiment 17, wherein one of $R^1$ and $R^2$ comprises a radiolabel and the other of $R^1$ and $R^2$ comprises a scintillant.

Embodiment 34

The method of embodiment 33, wherein detecting comprises performing a scintillation proximity assay.

Embodiment 35

The method of embodiment 1, wherein the reagent has a formula $R^1$-$A^1$-S—S-$A^2$-$R^2$; $R^1$ and $R^2$ are the same or different; at least one of $R^1$ and $R^2$ comprises a label; and at least one of $R^1$ and $R^2$ comprises an aryl group.

Embodiment 36

The method of embodiment 35, wherein the aryl group is selected from a phenyl group and a pyridinyl group.

Embodiment 37

The method of embodiment 1, wherein the ATPβS or GTPβS has a (βS) diastereomer content of at least about 80%, preferably at least about 90%, more preferably at least about 95%.

Embodiment 38

The method of embodiment 1, wherein the ATPβS or GTPβS has a (βR) diastereomer content of at least about 80%, preferably at least about 90%, more preferably at least about 95%.

Embodiment 39

The method of embodiment 1, wherein the substrate comprises a polypeptide.

Embodiment 40

The method of embodiment 1, wherein the substrate comprises a carbohydrate.

Embodiment 41

The method of embodiment 1, wherein the substrate comprises a nucleotide.

Embodiment 42

The method of embodiment 1, wherein the substrate comprises a fatty acid.

Embodiment 43

The method of embodiment 1, wherein the substrate comprises water.

Embodiment 44

The method of embodiment 17, wherein $R^1$ comprises a fluorophore and $R^2$ comprises a non-fluorophore.

Embodiment 45

The method of embodiment 44, wherein the fluorophore has an emission spectrum and the non-fluorophore has an absorption spectrum such that the emission spectrum and absorption spectrum overlap.

Embodiment 46

The method of embodiment 44, wherein the fluorophore and the non-fluorophore are present in the reagent at a distance of about 3-100 angstroms, preferably 3-75 angstroms, more preferably about 3-50 angstroms.

Embodiment 47

The method of embodiment 45 or 46, wherein detecting the at least one reaction product comprises observing dequenching of the fluorophore.

Embodiment 48

The method of any of embodiments 44-47, wherein the non-fluorophore comprises a chromophore.

Embodiment 49

The method of any of embodiments 44-48, wherein the non-fluorophore has a molecular weight that is at least about 2× the molecular weight of the fluorophore, and detecting comprises monitoring a decrease in fluorescence polarization of the fluorophore.

Embodiment 50

A method for identifying a test substance that inhibits kinase activity in a reaction mixture, the method comprising: (a) reacting the reaction mixture, the reaction mixture comprising: (i) the kinase; (ii) a substrate for the kinase; (iii) the test substance; (iii) ATPβS or GTPβS; (iv) a divalent cation that binds to ATPβS or GTPβS; (v) a reagent comprising at least one functional group that reacts with a thiol group of ADPβS or GDPβS and forms at least one reaction product; and (b) detecting the at least one reaction product.

Embodiment 51

The method of embodiment 50, wherein the test substance comprises a kinase inhibitor selected from the group consisting of bis-indoles, indolocarbazoles, phenylaminopyrimidines, balanoids, bis(indolyl)maleimides, pyridinylimidazoles, and mixtures thereof.

Embodiment 52

The method of embodiment 50, the reaction mixture further comprising a thiol-reducing agent.

Embodiment 53

The method of embodiment 52, the thiol-reducing agent comprising a phosphine.

Embodiment 54

The method of embodiment 53, the phosphine having the formula

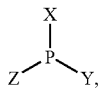

X, Y, and Z, independently are selected from the group consisting of —H, alkyl, alkenyl, alkynyl, aryl, and carboxyalkyl.

Embodiment 55

The method of embodiment 54, the phosphine comprising Tris(2-carboxyethyl)phosphine.

Embodiment 56

The method of embodiment 50, wherein detecting the at least one reaction product is performed contemporaneously as the at least one reaction product is formed.

Embodiment 57

The method of embodiment 50, wherein the at least one reaction product comprises a label.

Embodiment 58

The method of embodiment 57, wherein the label comprises a fluorophore, a chromophore, or both.

Embodiment 59

The method of embodiment 57, wherein the label comprises a fluorophore and a chromophore.

Embodiment 60

The method of embodiment 57, wherein the label comprises a fluorophore.

Embodiment 61

The method of embodiment 60, wherein the fluorophore comprises fluorescein or rhodamine.

Embodiment 62

The method of embodiment 60, wherein the fluorophore comprises pyrromethene boron difluoride.

Embodiment 63

The method of embodiment 60, wherein the fluorophore comprises a dansyl group.

Embodiment 64

The method of embodiment 57, wherein the label comprises a chromophore.

Embodiment 65

The method of embodiment 64, wherein the chromophore comprises 5-mercapto-2-nitrobenzoic acid.

Embodiment 66

The method of embodiment 50, wherein the reagent has a formula $R^1$—S—S—$R^2$; $R^1$ and $R^2$ are the same or different; and at least one of $R^1$ and $R^2$ comprises a label.

Embodiment 67

The method of embodiment 66, wherein the at least one reaction product has a formula selected from the group consisting of ADPβS-S—$R^1$, ADPβS-S—$R^2$, $R^1$—S—H, $R^2$—S—H, and salts thereof.

Embodiment 68

The method of embodiment 66, wherein $R^1$ comprises a first fluorophore and $R^2$ comprises a second fluorophore.

Embodiment 69

The method of embodiment 68, the first fluorophore having an emission spectrum and the second fluorophore having an absorption spectrum, such that the emission spectrum and the absorption spectrum overlap.

Embodiment 70

The method of embodiment 69, wherein the emission spectrum and the absorption spectrum overlap by at least about 10%, 20%, 30%, 40%, or 50%.

Embodiment 71

The method of embodiment 69, wherein the first fluorophore and the second fluorophore are present in the reagent at a distance of about 3-100 angstroms, preferably 3-75 angstroms, more preferably about 3-50 angstroms.

Embodiment 72

The method of embodiment 66, wherein $R^1$ and $R^2$ comprise identical fluorophores.

Embodiment 73

The method of embodiment 72, wherein detecting the at least one reaction product comprises observing a decrease in self-quenching.

Embodiment 74

The method of embodiment 68 or 72, wherein detecting the at least one reaction product comprises observing a change in fluorescence polarization.

Embodiment 75

The method of embodiment 68, wherein detecting the at least one reaction product comprises observing dequenching of the first fluorophore.

Embodiment 76

The method of embodiment 69, wherein detecting the at least one reaction product comprises observing a decrease in sensitized fluorescence of the second fluorophore.

Embodiment 77

The method of embodiment 66, wherein $R^1$ comprises a fluorophore having an emission spectrum and $R^2$ comprises a non-fluorophore having an absorption spectrum such that the emission spectrum and absorption spectrum overlap.

Embodiment 78

The method of embodiment 77, wherein the fluorophore and the non-fluorophore are present in the reagent at a distance of about 3-100 angstroms, preferably 3-75 angstroms, more preferably about 3-50 angstroms.

Embodiment 79

The method of embodiment 77, wherein detecting the at least one reaction product comprises observing dequenching of the fluorophore.

Embodiment 80

The method of embodiment 77, wherein the non-fluorophore comprises a chromophore.

Embodiment 81

The method of embodiment 66, wherein $R^1$ comprises a first fluorophore and $R^2$ comprises a second fluorophore, the second fluorophore having a molecular weight that is at least about 2× the molecular weight of the first fluorophore.

Embodiment 82

The method of embodiment 66, wherein one of $R^1$ and $R^2$ comprises a radiolabel and the other of $R^1$ and $R^2$ comprises a scintillant.

Embodiment 83

The method of embodiment 82, wherein detecting comprises performing a scintillation proximity assay.

Embodiment 84

The method of embodiment 50, wherein the reagent has a formula $R^1$-$A^1$-S—S-$A^2$-$R^2$; $R^1$ and $R^2$ are the same or different; at least one of $R^1$ and $R^2$ comprises a label; and at least one of $R^1$ and $R^2$ comprises an aryl group.

Embodiment 85

The method of embodiment 84, wherein the aryl group is selected from a phenyl group and a pyridinyl group.

Embodiment 86

The method of embodiment 50, wherein the ATPβS or GTPβS has a (βS) diastereomer content of at least about 80%, preferably at least about 90%, more preferably at least about 95%.

Embodiment 87

The method of embodiment 50, wherein the ATPβS or GTPβS has a (βR) diastereomer content of at least about 80%, preferably at least about 90%, more preferably at least about 95%.

Embodiment 88

The method of embodiment 50, wherein the substrate comprises a polypeptide.

Embodiment 89

The method of embodiment 50, wherein the substrate comprises a carbohydrate.

Embodiment 90

The method of embodiment 50, wherein the substrate comprises a nucleotide.

Embodiment 91

The method of embodiment 50, wherein the substrate comprises a fatty acid.

Embodiment 92

The method of embodiment 50, wherein the substrate comprises water.

Embodiment 93

The method of embodiment 50, wherein the thiol-reducing agent comprises beta-mercaptoethanol.

Embodiment 94

A kit for preparing a reaction mixture that is suitable for detecting kinase activity continuously, the kit comprising: (a) ATPβS or GTPβS; and (b) a reagent comprising at least one functional group that reacts with a thiol group of ADPβS or GDPβS and forms at least one reaction product.

Embodiment 95

The kit of embodiment 94, wherein the reagent has a formula $R^1$-$A^1$-S—S-$A^2$-$R^2$; $R^1$ and $R^2$ are the same or different; and at least one of $R^1$ and $R^2$ comprises a label.

Embodiment 96

The kit of embodiment 95, wherein at least one of $R^1$ and $R^2$ comprises a fluorophore.

Embodiment 97

The kit of embodiment 95, wherein at least one of $A^1$ and $A^2$ comprises an aryl group.

Embodiment 98

The kit of embodiment 94, further comprising a reducing agent.

Embodiment 99

The kit of embodiment 98, wherein the reducing agent comprises TCEP.

Embodiment 100

The kit of embodiment 98, wherein the reducing agent comprises beta-mercaptoethanol.

Embodiment 101

The kit of embodiment 94, further comprising a substrate for the kinase.

Embodiment 102

The kit of embodiment 94, further comprising a divalent cation that binds ATPβS or GTPβS, preferably a divalent metal cation such as $Mg^{2+}$, $Cd^{2+}$, $Co^{2+}$, $Cr^{2+}$, $Mn^{2+}$, and mixtures thereof.

Embodiment 103

The kit of embodiment 94, further comprising instructions for preparing the reaction mixture and detecting the at least one reaction product.

Embodiment 104

A kit comprising one or more components for performing the methods of any of embodiments 1-50.

Embodiment 105

A kit comprising one or more components for performing the methods of any of embodiments 50-93.

Embodiment 106

A method for detecting ATPase or GTPase activity in an aqueous reaction mixture comprising (a) reacting the reaction mixture, the reaction mixture comprising: (i) ATPβS or GTPβS; (ii) a divalent cation that binds to ATPβS or GTPβS; (ii) a reagent comprising at least one functional group that reacts with a thiol group of ADPβS or GDPβS and forms at least one reaction product; and (b) detecting the at least one reaction product.

Embodiment 107

The method of embodiment 106, the reaction mixture further comprising a thiol-reducing agent.

Embodiment 108

The method of embodiment 107, the thiol-reducing agent comprising a phosphine.

Embodiment 109

The method of embodiment 108, the phosphine having the formula

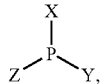

X, Y, and Z, independently are selected from the group consisting of —H, alkyl, alkenyl, alkynyl, aryl, and carboxyalkyl.

Embodiment 110

The method of embodiment 109, the phosphine comprising Tris(2-carboxyethyl)phosphine.

Embodiment 111

The method of embodiment 107, wherein the thiol-reducing agent comprises beta-mercaptoethanol.

Embodiment 112

The method of embodiment 106, wherein detecting the at least one reaction product is performed contemporaneously as the at least one reaction product is formed.

Embodiment 113

The method of embodiment 106, wherein the at least one reaction product comprises a label.

Embodiment 114

The method of embodiment 113, wherein the label comprises a fluorophore, a chromophore, or both.

Embodiment 115

The method of embodiment 113, wherein the label comprises a fluorophore and a chromophore.

Embodiment 116

The method of embodiment 113, wherein the label comprises a fluorophore.

Embodiment 117

The method of embodiment 116, wherein the fluorophore comprises fluorescein or rhodamine.

Embodiment 118

The method of embodiment 116, wherein the fluorophore comprises pyrromethene boron difluoride.

Embodiment 119

The method of embodiment 116, wherein the fluorophore comprises a dansyl group.

Embodiment 120

The method of embodiment 113, wherein the label comprises a chromophore.

Embodiment 121

The method of embodiment 120, wherein the chromophore comprises 5-mercapto-2-nitrobenzoic acid.

Embodiment 122

The method of embodiment 106, wherein the reagent has a formula $R^1$—S—S—$R^2$; $R^1$ and $R^2$ are the same or different; and at least one of $R^1$ and $R^2$ comprises a label.

Embodiment 123

The method of embodiment 122, wherein the at least one reaction product has a formula selected from the group consisting of ADPβS-S—$R^1$, ADPβS-S—$R^2$, $R^1$—S—H, $R^2$—S—H, and salts thereof.

Embodiment 124

The method of embodiment 122, wherein $R^1$ comprises a first fluorophore and $R^2$ comprises a second fluorophore or non-fluorophore.

Embodiment 125

The method of embodiment 124, the first fluorophore having an emission spectrum and the second fluorophore having an absorption spectrum, such that the emission spectrum and the absorption spectrum overlap.

Embodiment 126

The method of embodiment 125, wherein the emission spectrum and the absorption spectrum overlap by at least about 10%, 20%, 30%, 40%, or 50%.

Embodiment 127

The method of embodiment 125, wherein the first fluorophore and the second fluorophore are present in the reagent at a distance of about 3-100 angstroms, preferably 3-75 angstroms, more preferably about 3-50 angstroms.

Embodiment 128

The method of embodiment 122, wherein $R^1$ and $R^2$ comprise identical fluorophores.

Embodiment 129

The method of embodiment 128, wherein detecting the at least one reaction product comprises observing a decrease in self-quenching.

Embodiment 130

The method of embodiment 124 or 128 wherein detecting the at least one reaction product comprises observing a change in fluorescence polarization.

Embodiment 131

The method of embodiment 124, wherein detecting the at least one reaction product comprises observing dequenching of the first fluorophore.

Embodiment 132

The method of embodiment 125, wherein detecting the at least one reaction product comprises observing a decrease in sensitized fluorescence of the second fluorophore.

Embodiment 133

The method of embodiment 122, wherein $R^1$ comprises a fluorophore having an emission spectrum and $R^2$ comprises a non-fluorophore having an absorption spectrum such that the emission spectrum and absorption spectrum overlap.

Embodiment 134

The method of embodiment 133, wherein the fluorophore and the non-fluorophore are present in the reagent at a distance of about 3-100 angstroms, preferably 3-75 angstroms, more preferably about 3-50 angstroms.

Embodiment 135

The method of embodiment 133, wherein detecting the at least one reaction product comprises observing dequenching of the fluorophore.

Embodiment 136

The method of embodiment 133, wherein the non-fluorophore comprises a chromophore.

Embodiment 137

The method of embodiment 122, wherein $R^1$ comprises a first fluorophore and $R^2$ comprises a second fluorophore, the second fluorophore having a molecular weight that is at least about 2× the molecular weight of the first fluorophore.

Embodiment 138

The method of embodiment 122, wherein one of $R^1$ and $R^2$ comprises a radiolabel and the other of $R^1$ and $R^2$ comprises a scintillant.

Embodiment 139

The method of embodiment 138, wherein detecting comprises performing a scintillation proximity assay.

Embodiment 140

The method of embodiment 106, wherein the reagent has a formula $R^1$-$A^1$-S—S-$A^2$-$R^2$; $R^1$ and $R^2$ are the same or different; at least one of $R^1$ and $R^2$ comprises a label; and at least one of $A^1$ and $A^2$ comprises an aryl group.

Embodiment 141

The method of embodiment 140, wherein the aryl group is selected from a phenyl group and a pyridinyl group.

Embodiment 142

The method of embodiment 106, wherein the ATPβS or GTPβS has a (βS) diastereomer content of at least about 80%, preferably at least about 90%, more preferably at least about 95%.

Embodiment 143

The method of embodiment 106, wherein the ATPβS or GTPβS has a (βR) diastereomer content of at least about 80%, preferably at least about 90%, more preferably at least about 95%.

Embodiment 144

The method of embodiment 122, wherein $R^1$ comprises a fluorophore and $R^2$ comprises a non-fluorophore

Embodiment 145

The method of embodiment 144, wherein the fluorophore has an emission spectrum and the non-fluorophore has an absorption spectrum such that the emission spectrum and absorption spectrum overlap.

Embodiment 146

The method of embodiment 144, wherein the fluorophore and the non-fluorophore are present in the reagent at a distance of about 3-100 angstroms, preferably 3-75 angstroms, more preferably about 3-50 angstroms.

Embodiment 147

The method of embodiment 145 or 146, wherein detecting the at least one reaction product comprises observing dequenching of the fluorophore.

Embodiment 148

The method of any of embodiments 144-147, wherein the non-fluorophore comprises a chromophore.

Embodiment 149

The method of any of embodiments 134-148, wherein the non-fluorophore has a molecular weight that is at least about 2× the molecular weight of the fluorophore, and detecting comprises monitoring a decrease in fluorescence polarization of the fluorophore.

Embodiment 150

A method for identifying a test substance that inhibits ATPase or GTPβS activity in a reaction mixture, the method comprising: (a) reacting the reaction mixture, the reaction mixture comprising: (i) the ATPase or GTPase; (ii) the test substance; (iii) ATPβS or GTPβS; (iv) a divalent cation that binds ATPβS or GTPβS; (v) a reagent comprising at least one functional group that reacts with a thiol group of ADPβS or GDPβS and forms at least one reaction product; and (b) detecting the at least one reaction product.

Embodiment 151

A method for detecting GTPase activity of Gα subunit of G-protein, comprising: (a) reacting a reaction mixture, the mixture comprising: (i) Gα subunit of G-protein; (ii) GTPβS; and (iii) a reagent comprising at least one functional group that reacts with a thiol group of GDPβS and forms at least one reaction product; and (b) detecting the at least one reaction product.

Embodiment 152

The method of embodiment 151, the reaction mixture further comprising a divalent cation that binds GTPβS.

Embodiment 153

The method of embodiment 151 or 152, the reaction mixture further comprising one or more components that form natural or artificial membranes.

Embodiment 154

The method of any of embodiments 151-153, the reaction mixture further comprising detergent.

Embodiment 155

The method of any of embodiments 151-154, the reaction mixture further comprising a G-protein coupled receptor.

Embodiment 156

The method of any of embodiments 151-155, the reaction mixture further comprising Gβ subunit and Gγ subunit of G protein.

Embodiment 157

The method of any of embodiment 155 or 156, the reaction mixture further comprising a test substance suspected of having agonist or antagonist activity for the G-protein coupled receptor.

Embodiment 158

A method for identifying an agonist or antagonist of a G-coupled protein receptor, comprising: (a) contacting a G-coupled protein receptor complex with a test compound; (b) reacting a G subunit of the complex with GTPβS and a reagent comprising at least one functional group that reacts with a thiol group of GDPβS and forms at least one reaction product; and (c) detecting the at least one reaction product thereby identifying the agonist or antagonist.

Embodiment 159

A method for identifying a modulator of a G-protein coupled receptor, the method comprising contacting the G-protein coupled receptor with a test agent and detecting GTPase activity or the absence thereof, wherein detecting GTPase activity or the absence thereof comprises: (a) reacting a reaction mixture, the reaction mixture comprising: (i) Gα subunit of G-protein; (ii) GTPβS; (iii) a reagent comprising at least one functional group that reacts with a thiol group of GDPβS and forms at least one reaction product; and (b) detecting the at least one reaction product or the absence thereof thereby identifying the modulator of the G-protein coupled receptor.

Embodiment 160

The method of embodiment 159, wherein the reagent comprises a fluorophore, and optionally, detecting the at least one reaction product or the absence thereof comprises detecting a change in fluorescence of the fluorophore, and optionally, detecting is performed as the reaction product is formed.

Embodiment 161

A method for identifying a modulator of a G-protein coupled receptor complex, the method comprising: (a) reacting a mixture that comprises: (i) the complex; (ii) a test agent; (iii) GTPβS, GDPβS, or both; and (b) detecting GDPβS by reacting GDPβS and a reagent comprising at least one functional group that reacts with a thiol group of GDPβS and forms at least one detectable reaction product; thereby identifying the modulator of the G-protein coupled receptor complex.

Embodiment 162

The method of embodiment 161, the reaction mixture further comprising GTP, GDP, or both.

Embodiment 163

The method of embodiment 161 or 162, wherein the reaction mixture comprises GTPβS and detecting GDPβS comprises detecting GDPβS that is formed after GTPβS is hydrolyzed by Gα GTPase activity.

Embodiment 164

The method of embodiment 161 or 162, wherein the reaction mixture comprises GDPβS which binds to Gα to form a Gα-GDPβS complex and detecting GDPβS comprises detecting GDPβS that is released from the Gα-GDPβS complex.

Embodiment 165

A method for identifying a modulator of a G-protein coupled receptor complex, the method comprising: (a) reacting a mixture that comprises: (i) the complex; (ii) a test agent; and (iii) GDPβS; (b) removing GDPβS that is not bound to any protein of the complex; (c) adding GTP to the reaction mixture; (d) detecting GDPβS that is released from any protein of the complex by reacting the released GDPβS and a reagent comprising at least one functional group that reacts with a thiol group of the released GDPβS and forms at least one detectable reaction product; thereby identifying the modulator of the G-protein coupled receptor complex.

Embodiment 166

The method of embodiment 165, further comprising removing the released GDPβS from the reaction mixture prior to step (d).

The following examples are illustrative and not intended to limit the claimed subject matter.

EXAMPLES

Example 1

Synthesis of ATPβS (βR) Diastereomer

The ATPβS (βR) diastereomer may be synthesized as described in the art. (See, e.g., Eckstein and Goody, Biochemistry, Vol. 15, No. 8, 1976, pp. 1685-1691, incorporated by reference herein in its entirety). To an incubation mixture (volume 7.00 ml, containing 3.6 mM ADPβS, 7.2 mM $MgCl_2$, 72 mM Tris-HCl buffer, pH 8.0, 0.55 mM DTT, and 28.5 mM acetate phosphate) was added 425 U acetate kinase. The reaction was allowed to proceed for approximately 4 hr and was followed by TLC on PEI-cellulose using a 0.75 M $KH_2PO_4$ (pH 3.5) mobile phase. Purification was performed on a DEAE column using TEAB (triethylammonium bicarbonate) buffer. TEAB buffer was prepared by bubbling $CO_2$ gas into a 2 M solution of a triethylamine water mix until the pH dropped to between 7.6 and 7.8. The actual concentration of TEAB was determined by titrating with standardized HCl. The enzymatic synthesis reaction mixture was loaded on the DEAE column (1.5×10 cm), washed with 400 mL of 0.25 M to 0.5 M TEAB. The elution profile is provided in FIG. 5, with absorbance monitored at 260 nm collecting 13 ml fractions. The $^{31}P$ NMR spectrum for the diastereomer is shown in FIG. 6. Expected chemical shifts at pH 10 are αP (−11.5 ppm), βP (29-33 ppm), γP (−6.0 ppm).

Example 2

Synthesis of ATPβS (βS) Diastereomer

ATPβS (βS) diastereomer may be synthesized as described in the art. (See, e.g., Eckstein and Goody, Biochemistry, Vol. 15, No. 8, 1976, pp. 1685-1691, incorporated by reference herein in its entirety). To an incubation mixture (volume 17.15 ml, containing 1.36 mM ADPβS, 3.65 mM $MgCl_2$, 0.85 mM dithiothreitol, 380 mM KCl, 38 mM Tris-HCl, pH 8.0, 2.0 mM phosphoenolpyruvate, 2.4 mM NADH and 500 U lactate dehydrogenase was added 100 U pyruvate kinase. ATPβS was recovered by anion exchange chromatography on a Sephadex DEAE column. The $^{31}P$ NMR spectrum for the diastereomer is shown in FIG. 6.

Example 3

Chromogenic Assay Using $Ca^{2+}$-activated Myosin

A DTNB-coupled kinase assay was performed by reacting an assay mixture that included 10 mM DTNB and 5 mM $Ca^{2+}$. The myosin concentration in the assay mixture was 25 U/ml. Reaction with the DTNB reagent was measured by detecting changes in absorbance at λ-412 nm. A typical progress curve for a DTNB-coupled assay is shown in FIG. 7. A validation curve for $Ca^{2+}$-activated myosin's hydrolysis of the βS diastereomer of ATPβS using the DTNB-coupled assay is shown in FIG. 8. The variation of initial reaction rate (monitored at 412 nm) versus concentration of ATPβS (βS diastereomer as compared to βR diastereomer) is shown in FIG. 9.

For comparison, a PK/LDH-coupled assay was performed by reacting an assay mixture having the following composition: 20 μM NADH, 25 mM phosphoenolpyruvate, 10 U/ml LDH, 50 U/ml pyruvate kinase, 5 mM $Ca^{2+}$, 25 U/ml myosin. The variation of initial reaction rate (monitored at 340 nm) versus concentration of ATP using the PK/LDH-coupled assay is shown in FIG. 10.

Example 4

Chromogenic Studies Using Yeast Hexokinase

Hexokinase activity was verified by using a glucose-6-phosphate dehydrogenase (G6PDH)-coupled assay (340 nm) and a DTNB-coupled assay (412 nm). The G6PDH-coupled assay mixture had the following composition: 10 mM $MgCl_2$, 12 mM NADP$^+$, 11 U/ml G6PDH, 100 mM, pH 8.4 Tris-HCl buffer and 2.5 mM ATP. The DTNB-coupled assay mixture had the following composition: 10 mM MgCl$_2$, 10 mM DTNB, 10 mM glucose, 100 mM KCl, pH 7.0 HEPES buffer, 0.2 mM ATPβS (for the validation curve, see FIG. 11) and 50 U/ml hexokinase (for experiments in which ATPβS (βR) was varied (see FIG. 12).

Example 5

Comparison of ATP Versus ATPβS as a Phosphate Source for Myosin and Hexokinase $K_m$ and $V_{max}$ were calculated for myosin and hexokinase for kinase reactions that included ATP or the appropriate diastereomer of ATPβS as a phosphate source, and by fitting the saturation curve to the Michaelis-Menton equation. (see FIG. 13).

Example 6

Fluorogenic Studies Using Ca$^{2+}$-activated Myosin and Yeast Hexokinase

Fluorogenic dithio reagents (Bodipy® FL L-cystine or didansyl L-cystine, see FIG. 14) were used to detect ADPβS instead of DTNB under the general conditions for the DTNB-coupled assay for Ca$^{2+}$-activated myosin and yeast hexokinase. The general conditions of for the DTNB-coupled assay were followed except that the fluorogenic dithio reagents were present at concentration about 100 times lower than those concentrations of DTNB used. The fluorogenic dithio reagents (and the respective reaction products of the dithio reagents with ADPβS) were detected using a BMG Polarstar plate reader (at least 10 flashes per measurement). The results are displayed in FIG. 15 (Ca$^{2+}$-activated myosin) and FIG. 16 (yeast hexokinase). Validation curves for Ca$^{2+}$-activated myosin and yeast hexokinase are displayed in FIG. 17.

Example 7

Synthesis of a Sample R$^1$—S—S—R$^2$ Reagents Useful as Probes

A FRET probe with an aliphatic linker was synthesized from oxidized cystamine, according to the scheme in FIG. 18. Briefly, 0.3 mmol of Rhodamine B and 0.4 mmol of cystamine were reacted in a mixture of acetonitrile and chloroform (4:1) in the presence of 0.3 mmol BOP reagent and 5 mmol triethylamine. The resulting amide was purified by column chromatography (0.1 mmol) and reacted with 0.1 mmol of fluorescein isothiocyanide (FITC) in acetone at room temperature for 16 h. The final product was purified by column chromatography (11% overall yield). The compound was characterized by NMR and MALDI. In the first step, stoichiometry was carefully controlled to ensure that the dicystamine linker was labeled with only 1 equivalent of the rhodamine fluorophore.

Another type of the R$^1$—S—S—R$^2$ FRET probe, containing an aromatic linker, was prepared using a similar scheme to that shown in FIG. 18. DAPS (diaminodiphenyldisulfide) was used as starting compound, and contains thio and amino groups as para substituents on a benzene ring. The compound was designated Rh-DAPS-FITC (alternatively referred to as R-DAPS-F or F-DAPS-R herein).

Example 8

Analysis of the pH Defendant Behavior of the R$^1$—S—S—R$^2$ Reagent

The aromatic linker (DAPS) version of the FRET reagent is shown in FIG. 19, in structures that predominate at high and low pH extremes. The structure of Rh-DAPS-FITC is shown as it would appear at acidic pH in (a), while the structure of Rh-DAPS-FITC at basic pH is shown in (b). The cyclized forms of the fluorophores have decreased fluorescence. The fluorescence emission spectrum (excitation at 495 nm, for fluorescein) of 5 μM Rh-DAPS-FITC at different pH's is shown in panel (c). The predominant emission spectrum for fluorescein is at 520 nm. The small FRET effect observed at lower pH, where the rhodamine fluorophore more highly populates the open conformation, may indicate that a pH independent version of R$^1$ and R$^2$ will produce a much stronger FRET effect for the reagent. The form of the reagent in this example may be suitable for monitoring the removal of quenching by reduction of the dithio group. The pH independent form of the reagent may be suitable for monitoring the decrease of FRET (sensitized emission by the rhodamine fluorophore).

Example 9

Selective Reaction of ADPβS Versus ATPβS and F-DAPS-R and Use in Kinase Coupled Assay ADPβS (or ATPβS), 500 μM, was added to F-DAPS-R (1 μM) in 96 well plates. Fluorescence emission from the donor was analyzed (Ex: 485 nm, Em: 520 nm) over time (0-45 minutes), using a POLARstar Galaxy FP plate reader. (See FIG. 20). Dequenching was observed for the reaction with ADPβS, while no reaction was observed with ATPβS. A comparison of a thiol-based coupled kinase assay and the commonly used pyruvate kinase/lactate dehydrogenase-coupled kinase assay (PK/LDH assay) is shown in FIG. 21. Change in absorption properties of the donor fluorophore, upon reduction of the dithio group, are indicated in FIG. 21D.

Example 10

Monitoring the GTPase Activity of GPCRs using GTPβs in Dithio-coupled Assays

Dithio-coupled assays may be used to monitor GTP hydrolysis where GTPβS is used in place of GTP (see FIGS. 22 and 23). Production of GDPβS is monitored where it reacts selectively with dithio reagents (as compared to GTPβS), such as DTNB or fluorescent DSSA reagents (FIG. 24). Suitable dithio detection reagents for detecting GDPβS are presented in FIG. 24. The reaction is monitored by measuring an increase in fluorescence or other signal, as the dithio detection reagent is reduced. (See FIG. 23 for exemplary assay.) The activation state of a GPCR may be determined by detecting Gα-catalyzed GTP hydrolysis. The GPCR or a complex that includes GPCR may be present in a membrane system that includes components that form natural or artificial membranes (e.g., amphiphilic fatty acids), or the GPCR or complex that includes GPCR may be solubilized (e.g., in a detergent solution such as a non-ionic detergent solution or an ionic detergent solution). For example, the GPCR or a complex that includes GPCR may be bound either to a plasma membrane, or to a detergent or micelle, to simulate a membrane-like environment. The assay may be performed in intact cells, cell extracts, or in a purely in vitro reconstituted system using detergent (e.g., a non-ionic detergent such as Triton® X-100 detergent or an ionic detergent such as SDS).

In an example of this assay, Histamine H1 antagonists are identified by expressing $H_1R$ plus RGS in Sf9 cells. Membranes are dissolved in buffer (0.1 mM EDTA, 100 mM Tris, pH 7.4, 1 mM $MgCl_2$, 0.1 mM ATP, 1 mM adenylyl imidophosphate, 50 μg creatine kinase, 5 mM creatine phosphate, 0.2% bovine serum albumin). Assays are preformed in a 0.5 mL volume with 5-200 μg of protein present, incubating at 25° C. for 60-90 minutes (250 rpm) with 1 μM histamine agonist and varied antagonist (1 nM to 20 μM, depending on expected $IC_{50}$) to generate dose-response curves. Anywhere from 0.1 to 500 μM GTPβS is then added along with either 1-20 μM DSSA fluorescent dithio reagent (FIG. 24), or 0.5 mM DTNB (FIG. 23). The assay may be a continuous assay (i.e., with "real-time" detection), a steady state assay, or a fixed time assay that utilizes quenching of the reaction and reading of fluorescence.

It will be readily apparent to one skilled in the art that varying substitutions and modifications may be made to the invention disclosed herein without departing from the scope and spirit of the invention. The invention illustratively described herein suitably may be practiced in the absence of any element or elements, limitation or limitations which is not specifically disclosed herein. The terms and expressions which have been employed are used as terms of description and not of limitation, and there is no intention in the use of such terms and expressions of excluding any equivalents of the features shown and described or portions thereof, but it is recognized that various modifications are possible within the scope of the invention. Thus, it should be understood that although the present invention has been illustrated by specific embodiments and optional features, modification and/or variation of the concepts herein disclosed may be resorted to by those skilled in the art, and that such modifications and variations are considered to be within the scope of this invention.

In addition, where features or aspects of the invention are described in terms of Markush groups or other grouping of alternatives, those skilled in the art will recognize that the invention is also thereby described in terms of any individual member or subgroup of members of the Markush group or other group.

Also, unless indicated to the contrary, where various numerical values are provided for embodiments, additional embodiments are described by taking any 2 different values as the endpoints of a range. Such ranges are also within the scope of the described invention.

What is claimed is:

1. A method for detecting a thiol-containing nucleotide diphosphate in a reaction mixture, the method comprising adding to the mixture a fluorescent reagent comprising at least one functional group that reacts with the thiol group of the nucleotide diphosphate, the fluorescent reagent exhibiting a change in fluorescence after reacting with the thiol group of the nucleotide diphosphate, thereby detecting the nucleotide diphosphate in the reaction mixture, wherein the fluorescent reagent has a formula $R^1$—S—S—$R^2$, $R^1$ and $R^2$ are the same or different, and at least one of $R^1$ and $R^2$ comprises a fluorophore.

2. The method of claim 1, wherein the thiol-containing nucleotide diphosphate is GDPβS or ADPβS.

3. The method of claim 1, wherein the reaction mixture further comprises:
   (i) a GTPase; and
   (ii) GTPβS.

4. The method of claim 3, wherein the GTPase is present in a G-protein coupled receptor complex.

5. The method of claim 4, where the reaction mixture further comprises:
   (iii) a test agent for modulating the activity of the complex.

6. The method of claim 1, wherein the reaction mixture further comprises:
   (i) an ATPase; and
   (ii) ATPβS.

7. The method of claim 1, wherein the reaction mixture further comprises:
   (i) a kinase;
   (ii) ATPβS;
   (iii) a divalent cation that binds ATPβS; and
   (iv) a substrate for the kinase.

8. The method of claim 1, the reaction mixture further comprising a thiol-reducing agent.

9. The method of claim 8, the thiol-reducing agent comprising a phosphine.

10. The method of claim 1, wherein the change in fluorescence of the fluorescent reagent is detected contemporaneously as the change in fluorescence of the fluorescent reagent occurs.

11. The method of claim 1, wherein the thiol-containing nucleotide diphosphate is GDPβS or ADPβS.

12. The method of claim 1, wherein the reaction mixture further comprises:
   (i) a GTPase; and
   (ii) GTPβS.

13. The method of claim 12, wherein the GTPase is present in a G-protein coupled receptor complex.

14. The method of claim 13, where the reaction mixture further comprises:
   (iii) a test agent for modulating the activity of the complex.

15. The method of claim 1, wherein the reaction mixture further comprises:
   (i) an ATPase; and
   (ii) ATPβS.

16. The method of claim 1, wherein the reaction mixture further comprises:
   (i) a kinase;
   (ii) ATPβS;
   (iii) a divalent cation that binds ATPβS; and
   (iv) a substrate for the kinase.

17. The method of claim 1, the reaction mixture further comprising a thiol-reducing agent.

18. The method of claim 17, the thiol-reducing agent comprising a phosphine.

19. The method of claim 1, wherein $R^1$ comprises a first fluorophore and $R^2$ comprises a second fluorophore.

20. The method of claim 19, wherein the first fluorophore and second fluorophore are different.

21. The method of claim 1, wherein $R^1$ comprises a fluorophore and $R^2$ comprises a quencher.

* * * * *